US007086288B2

(12) United States Patent
Lee et al.

(10) Patent No.: US 7,086,288 B2
(45) Date of Patent: Aug. 8, 2006

(54) THIN MEMBRANE TRANSDUCER

(75) Inventors: Junghoon Lee, Wilmette, IL (US); JaeHyun Chung, Evanston, IL (US); Kyong-Hoon Lee, Wilmette, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 10/723,307

(22) Filed: Nov. 26, 2003

(65) Prior Publication Data
US 2004/0211251 A1  Oct. 28, 2004

Related U.S. Application Data

(60) Provisional application No. 60/429,879, filed on Nov. 27, 2002.

(51) Int. Cl.
*G01L 9/12* (2006.01)
(52) U.S. Cl. ...................................................... 73/718
(58) Field of Classification Search ............ 73/204.26, 73/754, 720, 721, 722, 727, 777, 715, 718, 73/724; 600/347, 345, 364, 365
See application file for complete search history.

(56) References Cited

U.S. PATENT DOCUMENTS

| 4,864,463 | A | * | 9/1989 | Shkedi et al. ................. 73/718 |
| 6,050,138 | A | | 4/2000 | Lynch et al. ............... 73/150 A |
| 6,201,980 | B1 | | 3/2001 | Darrow et al. .............. 600/347 |
| 6,480,730 | B1 | * | 11/2002 | Darrow et al. .............. 600/347 |
| 6,647,796 | B1 | * | 11/2003 | Beach et al. ................. 73/754 |
| 2001/0016683 | A1 | | 8/2001 | Darrow et al. .............. 600/347 |
| 2004/0096357 | A1 | | 5/2004 | Majumdar et al. ............ 422/57 |
| 2004/0152211 | A1 | | 8/2004 | Majumdar et al. ........... 436/518 |

OTHER PUBLICATIONS

Wu et al., "Origin of Nanomechanical Cantilever Motion Generated from Biomolecular Interactions," Proceedings of the National Academy of Science, 98 (4), 2001, pp. 1560-1564.
Lin et al., "Surface Stress Curves for Gold," J. Electrochem. Soc., 123, Aug. 1976, pp. 1145-1151.
Lee, "Microactuation by Continuous Electrowetting and Electrowetting: Theory, Fabrication, and Demonstration," Dissertation, University of California, Los Angeles, 2000, pp. 1-173.
Lundbaek et al., "Lipid E Stress, and Assembly of Gramicidin Channels," Biotechnology, 36, 1997, pp. 5695-5701.
Fritz et al., "Translating Biomolecular Recognition into Nanomechanics," Science, vol. 288, 2000, pp. 316-318.
Wu et al., "Bioassay of prostate-specific antigen (PSA) using microcantilevers," Nature Biotechnology, vol. 19, 2001, pp. 856-860.
Subramanian et al., "Glucose biosensing using an enzyme-coated microcantilever," Applied Physics Letters, 81 (2) , 2002, pp. 385-387.

(Continued)

Primary Examiner—Harshad Patel

(57) ABSTRACT

A transducer includes a substrate and a thin membrane having a shape that can be deflected relative to the substrate to provide an amount of membrane deflection useful for sensing or actuation purposes.

20 Claims, 22 Drawing Sheets

No binding occurs

Specific binding

OTHER PUBLICATIONS

Hagan et al., "Nanomechanical Forces Generated by Surface Grafted DNA," Journal of Physical Chmistry, B 106, 2002, pp. 10163-10173.

Thaysen et al., "Su-8 Based Piezoresistive Mechanical Sensor," IEEE Workshop on MEMS, 2002, pp. 320-323.

Lin et al., "Surface Stress Curves for Gold," J. Electrochem. Soc., 123, 1976, abstract only.

Lee et al., "SPR Imaging Measurements of 1-D and 2-D DNA Microarrays Created from Microfluidic Channels on Gold Thin Films," Anal. Chem., vol. 73, No. 22, 2001, pp. 5525-5531.

Savran et al., "Fabrication and Characterization of a Micromechanical Sensor for Differential Detection of Nanoscale Motions," J. of Microelectromechanical Systems, vol. 11, No. 6, 2002, pp. 703-708.

Berger et al., "Surface Stress in the Self-Assembly of Alkanethiols on Gold," Science, vol. 276, 1997, pp. 2021-2024.

Bowden et al., "Spontaneous formation of ordered structures in thin films of metals supported on an elastomeric polymer," Nature, 393, 1998, pp. 146-149.

Hansen et al., "Cantilever-Based Optical Deflection Assay for Discrimination of DNA Single-Nucleotide Mismatches," Anal. Chem., 73 (7), 2001, pp. 1567-1571.

Thaysen et al., "Cantilever-based bio-chemical sensor integrated in a microliquid handling system," IEEE Workshop on MEMS, 2001, pp. 401-404.

* cited by examiner

Thickness of the membrane : t

No binding occurs

Specific binding $$C_{overall} = \Delta C_{individual} \times (n \times n)$$

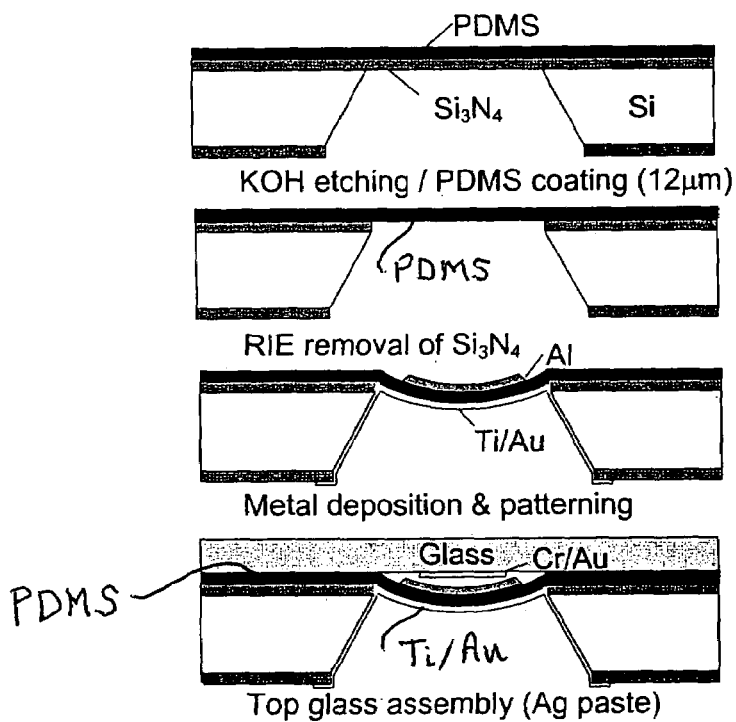
Fig. 34a KOH etching / PDMS coating (12μm)
Fig. 34b RIE removal of Si₃N₄
Fig. 34c Metal deposition & patterning
Fig. 34d Top glass assembly (Ag paste)
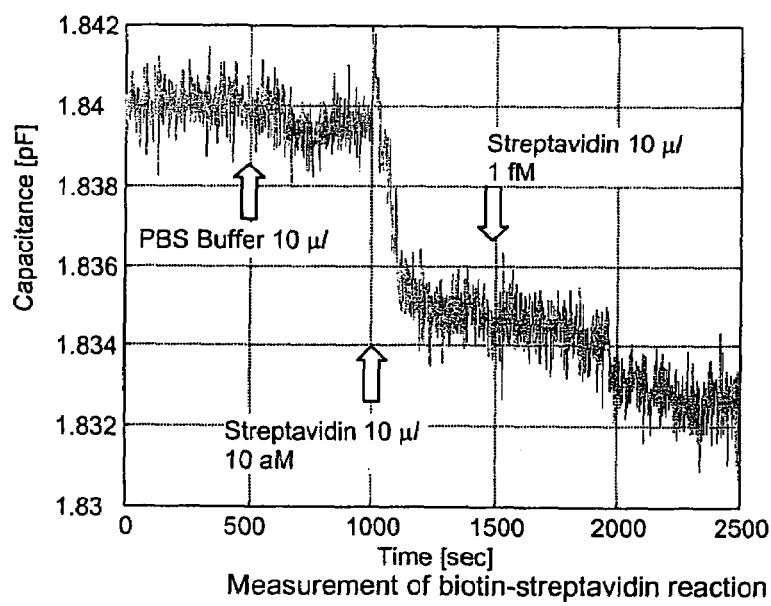
Measurement of biotin-streptavidin reaction
Fig. 35

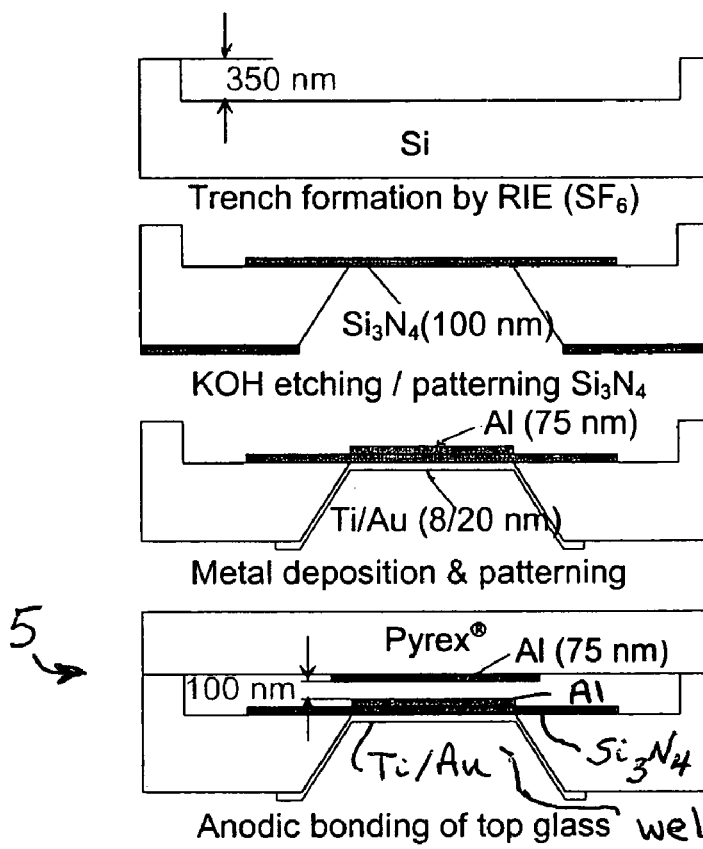
Fig. 36a — Trench formation by RIE (SF$_6$)
Fig. 36b — KOH etching / patterning Si$_3$N$_4$
Fig. 36c — Metal deposition & patterning
Fig. 36d — Anodic bonding of top glass well
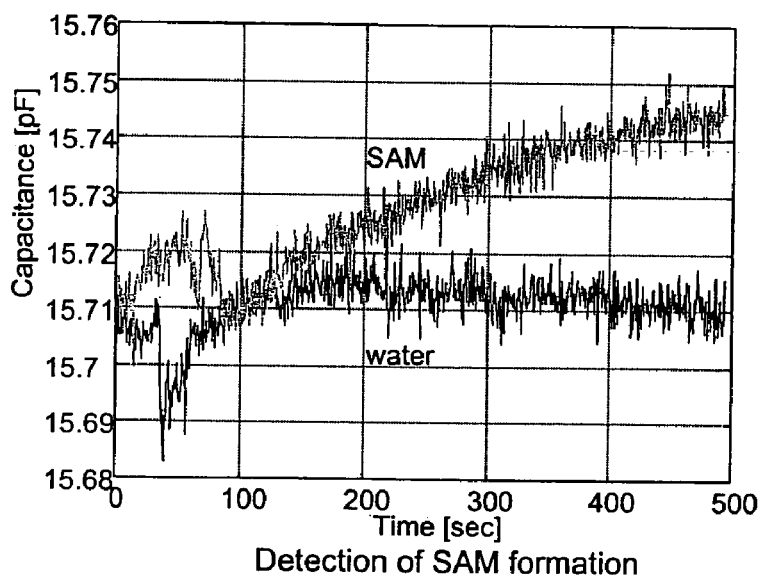
Fig. 37 — Detection of SAM formation

THIN MEMBRANE TRANSDUCER

This application claims the benefits and priority of provisional application Ser. No. 60/429,879 filed Nov. 27, 2002.

FIELD OF THE INVENTION

The present invention relates to a thin membrane transducer and products such as sensors, actuators and others that embody one or more transducers, as well as a method of their manufacture.

BACKGROUND OF THE INVENTION

In MEMS (micro electro mechanical systems) or micro systems technology (MST), sensors and actuators have been developed based on micro-cantilever technology wherein mechanical conversion of chemical or biomolecular events is employed. For example, it has been reported that a thin micro-cantilever bends due to surface stress change caused by a specific biomolecular reaction such as DNA hybridization. In addition, a thin film of gold foil has been demonstrated to change its length due to an ionic adsorption by surface stress induced by an electrochemical reaction.

There are advantages enabled by this micro-cantilever approach over conventional dye and other sensing methods. In micro-cantilever technology, for example, a biomolecular reaction can be detected without tagging molecules with optically observable chemicals such as dye or fluorescent particles. It is also considered possible that many micro-cantilevers can be coated with different-chemical binding-sites in order to obtain multiple answers with single testing. It may also be possible that many micro-cantilevers can be coated with different chemical binding sites and multiple detection can be made for one sample introduced to react with different micro-cantilevers. There are, however, certain difficulties and limits of this micro-cantilever based method as listed below; namely:

Detection limit
Cost of detection
Detection time
Multiple detections
Linearity and dynamic range Detection limit: The amount of cantilever bending is extremely small, in the range of 10–100 nm. A sensing method such as optical detection that can resolve a fraction of a nanometer is required. Nevertheless, the best detection limit of the method is above 10 nM range in biomolecular concentration according to literature. In contrast, optical detection based on light sensitive particles such as laser induced fluorescence can sense 1 pM range. Use of soft material such as SU-8 plastic cantilever, was considered to improve the detection limit problem. The thickness of the plastic cantilever beam, however, had to be increased, and this approach resulted in a poor detection limit. Even if a thinner plastic cantilever structure is used for better detection limit, the cantilever structure will be too flexible to maintain its shape in a fluid.

Cost of detection: An optical detection method needs to be used to maintain the detection limit of existing approaches. A laser source based detection system is be integrated with the micro-cantilever samples. The overall system becomes bulky and complicated in this case. Multiple laser sources are needed for multiple detection, adding to the cost and complexity. Furthermore, this system cannot be used with optically non-transparent solutions such as blood. Piezoresistive elements can be integrated with the micro-cantilevers in order to overcome the problems mentioned here. However, the detection limit by this method is even worse compared to conventional methods such as optical detection.

Detection time: Flexible micro-cantilevers submerged in a liquid solution will undergo a significant fluctuation in their shapes due to very small fluid disturbance. Accordingly, a sufficient time is needed for settling down the fluctuation. Introduction of the sample for detection needs to be done with extreme care, and the sample solution is injected from some distance from the cantilevers. The reaction time afterwards is strictly limited by diffusion of molecules to the cantilevers. This process without any help of mixing flow is very slow and inefficient. As a result, it takes very long for a typical detection, on the order of hours.

Multiple detection: One of the major advantages claimed by the use of micro-cantilevers is the possibility of detecting many reactions with one analyte solution. To achieve this goal, it is required to fabricate many cantilevers in a batch fashion. This has been achieved by using photolithography-based microfabrication. It is also important to coat different beams with different molecules to obtain multiplexed reaction signals. The coating process, however, is extremely difficult with any of the present methods when many cantilevers (e.g., hundreds) are required to be coated with different molecules. Photolithography-based synthesis of molecules (e.g., Affimetrix approach) are difficult to carry out because the completed cantilever structures are too flexible. Various kinds of stamping techniques (e.g., Cartesian DNA microarray) cannot be used for this same reason because the flexible cantilevers will be attached on the substrate after the solution is dried. Use of multiple light source also limits the number of detectable cantilevers available. It would be an extremely difficult and time consuming task to integrate and calibrate many laser light sources.

SUMMARY OF THE INVENTION

An embodiment of the present invention provides a thin membrane transducer and method which overcome one or more of the above disadvantages of cantilever based systems.

The present invention envisions in one embodiment a transducer comprising a substrate and a thin membrane having a particular shape that can be deflected relative to the substrate to provide an amount of membrane deflection useful for sensing or actuation purposes. The membrane may be deflected as a result of surface stress induced by an interaction with a medium.

In an illustrative embodiment of the invention, a sensor comprises a substrate and thin membrane peripherally connected to the substrate wherein the membrane has a dome shape and includes a reaction agent on an exterior surface where a reaction with a species, such as molecules, of an analyte (medium) can occur in a manner to deflect the membrane relative to the substrate. The thin membrane may be an elastomeric material or any other material. Means is provided for detecting deflection of the membrane relative to the substrate. For example, in a particular illustrative embodiment of the present invention, a capacitance detection device is provided to detect a change in capacitance caused by the deflection of the thin membrane. The reaction agent may comprise a coating on the exterior membrane surface that includes molecules providing chemical and/or biomolecular reaction sites. The present invention also envisions a sensor that includes at least one sensor of the type described and at least one similar sensor without the reaction agent to provide a reference relative to which a differential deflection of the sensor membrane caused by the chemical and/or biomolecular reaction may be compared.

In a further illustrative embodiment of the present invention, the thin membrane includes an interior surface subjected to gas pressure to impart and maintain a working convex dome shape thereto. For this embodiment, the present invention envisions a sensor that includes a sensing membrane embodying features of the sensor described above and an actuation membrane that is movable by electrostatic force in a manner to gas pressurize the sensing membrane when the actuating membrane is moved toward the substrate so as to impart and maintain the convex dome shape thereto. Alternately, in another illustrative embodiment of the present invention, the thin membrane includes one or more metallic layers applied on the membrane in a manner to maintain a convex or concave shape imparted to the membrane by heat and/or plastic deformation during fabrication of the membrane. A membrane with a self-supporting convex or concave shape is thereby provided and avoids the need to gas pressurize the membrane to impart a shape thereto.

The present invention also envisions an actuator that includes a substrate and an actuation membrane spaced by a gas-containing gap from the substrate wherein the actuation membrane is movable toward the substrate to expel gas under pressure from the gap.

Other aspects of the invention relate to methods embodying the above features of the invention.

A particular aspect of the present invention provides a method of forming a thin membrane having a self-supporting convex or concave dome shape comprising the steps of heating the membrane to impart the dome shape thereto, depositing one more metallic layers on the heated membrane, and cooling the membrane to ambient temperature, the membrane being constrained by the one or more metallic layers in the dome shape.

The above and other advantages of the present invention will become more readily apparent from the following detailed description taken with the following drawings.

DESCRIPTION OF THE DRAWINGS

FIGS. 34a, 34b, and 34c schematically illustrate steps to fabricate a self-supporting dome shaped elastomeric membrane pur and FIG. 34d schematically illustrates a sensor of the invention made by cooperatively disposing a glass substrate with a Au layer electrode facing the dome shaped membrane.

FIG. 35 is a graph of capacitance of a prototype sensor of the invention versus time during measurement of biotin-streptavidin reaction.

FIGS. 36a, 36b, and 36c schematically illustrate steps to fabricate a self-supporting hard silicon nitride membrane pursuant to an aspect of the invention and FIG. 36d schematically illustrates a sensor of the invention made by cooperatively disposing a glass substrate with an Al electrode facing the hard membrane.

FIG. 37 is a graph of capacitance of the prototype sensor of FIG. 36d versus time during detection o SAM.

DESCRIPTION OF THE INVENTION

Figure 20A:
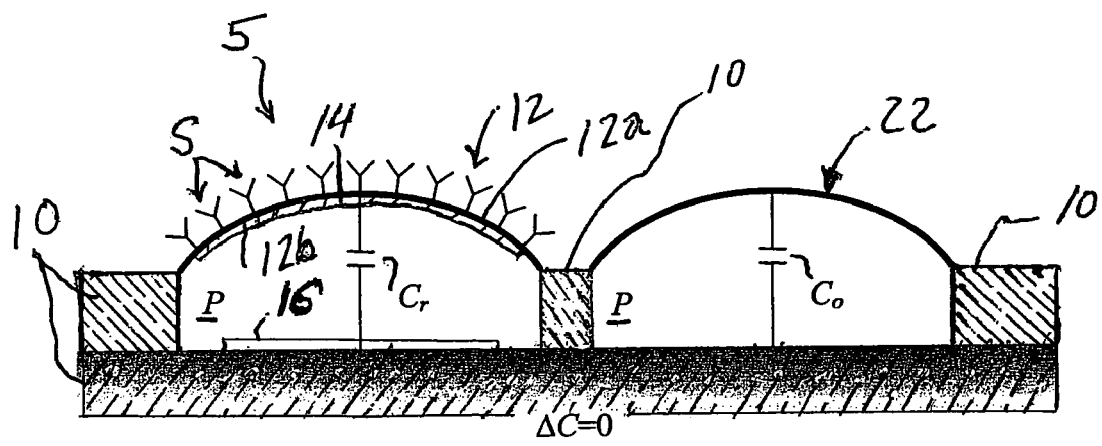
FIG. 20a is a schematic view of a sensor with two thin-PDMS membranes, one with reaction sites and the other without reaction agent, for differential measurement of capacitance change due to surface stress with no binding at the reaction sites.
Figure 20B:
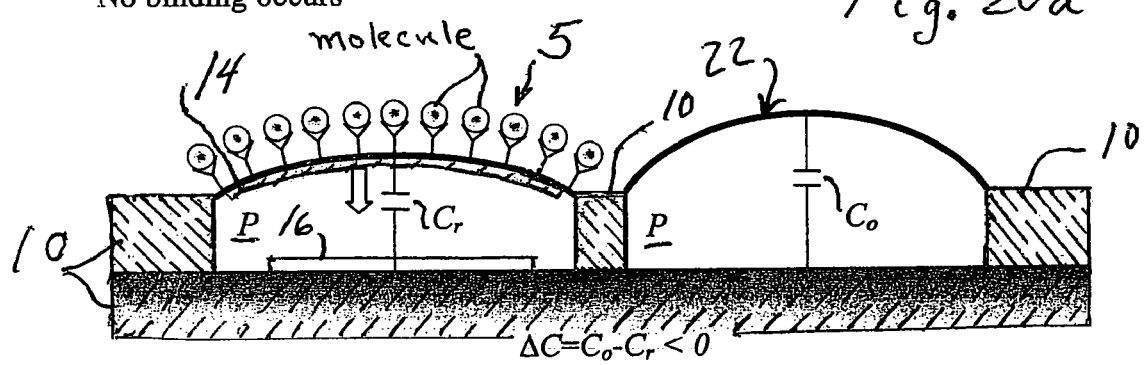
FIG. 20b is similar to FIG. 20a but with chemical or biomolecular binding at the reaction sites.
Figure 33A:
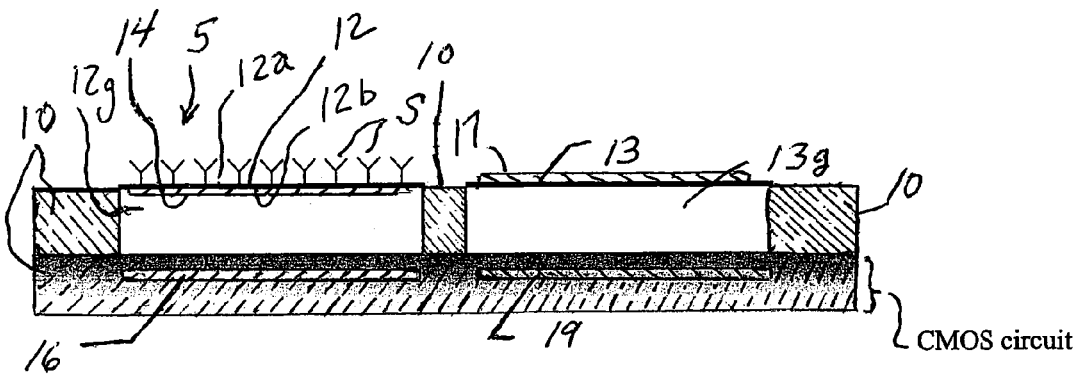
FIGS. 33a and 33b are schematic sectional views of a sensor having a sensor area and actuation area before and after actuation of the actuation membrane, respectively.
Figure 33B:
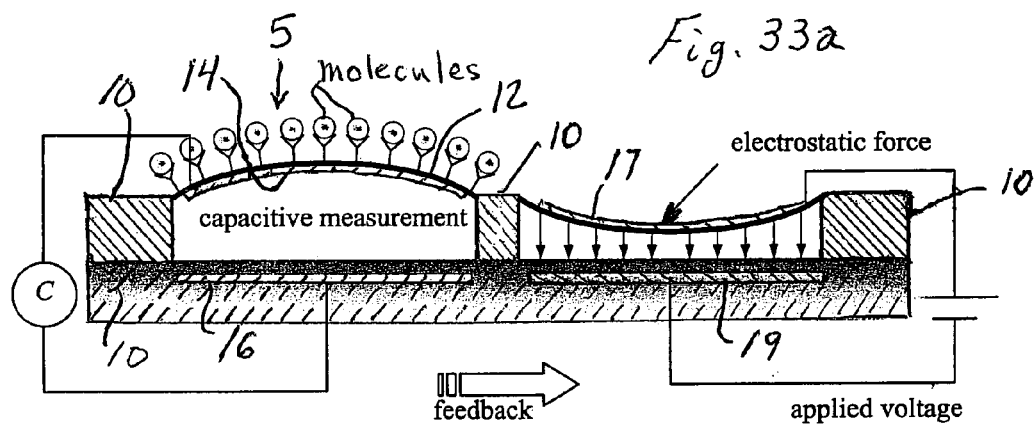

The present invention provides in one embodiment a thin membrane transducer 5 having one or more substrates 10 and a thin membrane 12 having a particular convex or concave shape with an inner (e.g. center) region thereof spaced from the substrate 10 by a small space or gap and movable relative to the substrate to provide a membrane deflection useful for sensing or actuation purposes, FIGS. 20b and 33b. For purposes of illustration and not limitation, a transducer pursuant to the invention can be used as an ultra sensitive sensor or as a large deflection actuator. An illustrative sensor includes, but is not limited to, a biomolecular sensor or chemical sensor wherein there is a direct mechanical conversion of chemical, biomolecular or other interaction event, a high sensitivity mechanical sensor such as a pressure sensor, accelerometer, and gyroscope or an image sensor such as an infrared sensor. An illustrative actuator includes, but is not limited to, an electromechanical actuator such as a micro air pump, RF (radio frequency) component, and image projector.

The substrate 10 may be provided as separate substrate sections joined together or as a single substrate and can comprise any suitable material including, but not limited to, ceramic, glass, plastic and others. The outer peripheral edges of the thin membrane 12 are connected to or fastened on the substrate 10. In particular, the outer peripheral edges of the membrane are peripherally connected to the substrates by adhesive, or permanent bonding, leaving the inner region of the thin membrane 12 free to move relative to the substrate.

The thin membrane can comprise any material including, but not limited to, a plastic elastomer such as rubber, latex, and polydimethylsiloxane (PDMS) or other polymer which have low mechanical stiffness and large deflectability as well as hard ceramic materials such as $SiO_2$, $Si_2N_3$ and others which high mechanical stiffness and relatively low deflectability as compared to elastomers. The membrane can comprise any material that can be fabricated to provide a thin membrane of desired shape. The thin membrane can be fabricated to provide extreme deflectability (flexibility) associated with a very thin elastomer membrane and/or extreme sensitivity of a very small gap membrane. Plastic elastomers such as rubber, latex, and PDMS that exhibit very small mechanical stiffness and allow very large deformation can be used in many applications where large deflection is necessary. In order to achieve large deflection or high sensitivity, a thin membrane of the appropriate material is used wherein membrane thickness is in the range of 1–100 μm and preferably in the range of about 10 μm or less. For high sensitivity detection, a small gap between the peripheral region of the shaped membrane 12 and the substrate 10 may be provided, a gap of about 1 μm or less may be provided to this end. An extremely small gap of 50 nm (nanometers) or less can be used for extreme sensitivity. The performance or operating characteristics of thin membrane transducers depend on membrane thickness, gap size between membrane and substrate, size and shape of membrane, and material properties such as stiffness and Poisson's ratio. Fabrication of thin arcuate, dome-shaped membranes by various methods is described later in detail.

Figure 31:
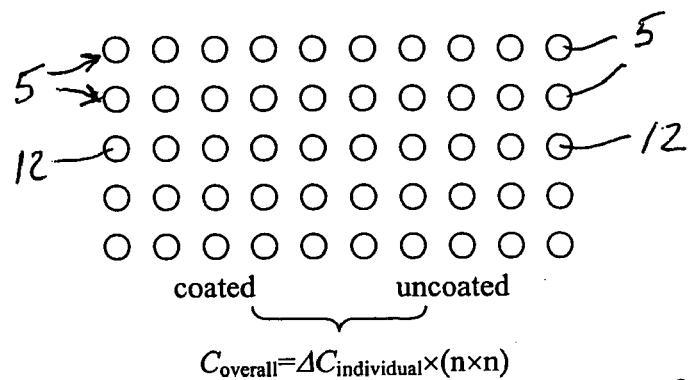
FIG. 31 is a schematic view of an array of sensors to improve sensitivity of detection.
Figure 32:
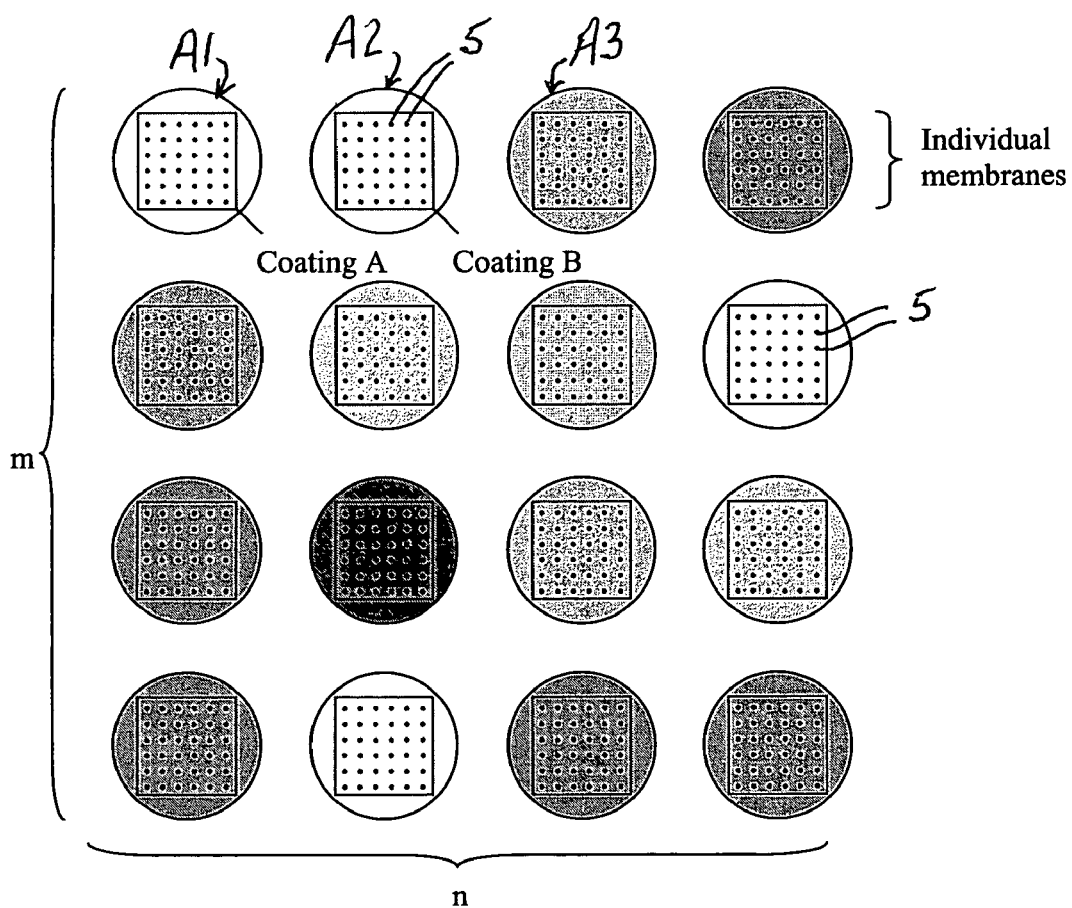
FIG. 32 is a schematic view of a multi-array of sensors to provide multiple detection.

An embodiment of the invention for use in detecting a chemical or biomolecular reaction occurring between a species, such as molecules, ions, and the like, of an analyte and binding or reaction sites on thin dome-shaped membrane 12 will now be described for purposes of illustration and not limitation. The analyte can be a liquid or a gas containing the introduced analyte species to be detected. The analyte may be flowed across the membrane surface 12a in a direction generally parallel to the substrate 10 driven by external pumping or micropumps integrated with the device or placed in one or more wells provided on the sensor as described below. Unlike micro-cantilevers, the convex or concave membrane is robust against the flow over it, and will maintain its shape or quickly recover the shape after a strong flow disturbance. Furthermore, the flow disturbance, if any, will simultaneously affect the two membranes adjacent to each other, and the noise due to the flow effect can be eliminated by comparing the signals from coated and uncoated membranes. The binding or reaction sites can be provided on the thin membrane 12 by coating its outer convex surface 12a with a coating including appropriate molecules to provide chemical and/or biomolecular binding and/or reaction sites as shown in FIGS. 31, 32, and 33. Appropriate binding or reaction sites alternatively can be provided by lithography or other techniques.

A thin dome-shaped membrane 12 is shown being employed for detecting surface stress change due to chemical or biomolecular reaction occurring between the introduced molecules of the analyte (medium) and the reaction site molecules coated on the convex surface 12a of the membrane 12. The invention is not limited to chemical or biomolecular reactions since other interactions, such as adsorption, hydrogen bonding, deposition, self-assembly of molecular structures, thermal events, and the like, between a medium and an agent on the membrane surface 12a or the membrane surface 12a itself that will induce membrane surface stress that produces a deflection of the membrane can be sensed or detected in practice of the invention. FIGS. 1–16 illustrate membrane stress and deflection analyses when the inner membrane surface 12b subjected to internal gas pressure at a pressure P and without and with a specific interaction such as binding or reaction occurring between molecules coated on the convex membrane surface 12a and the introduced molecules of the analyte such that surface stress at convex membrane surface 12a will change in a compressive sense as a result. The inflation of the membrane increased (w>0 where w is a deflection of membrane at the center) with the same pressure difference due to the reduction of pressure-induced tensile stress in the membrane by additional the compressive stress from surface reaction. If the induced stress is tensile then, the amount of inflation or the deflection of membrane will decrease (i.e., w<0) due to the increase of pressure-induced tensile stress in the membrane by the additional tensile stress from surface reaction. FIGS. 17–30 illustrate detecting the deflection of the thin membrane 12 via measurement of capacitance between electrode associated with the thin membrane 12 and the substrate 10, the change in capacitance providing a means for detecting the surface stress at convex membrane surface 12a resulting from the interaction, e.g. the chemical and/or biomolecular reaction. Detection of the change in capacitance thereby provides a means for detecting the occurrence of the chemical and/or biomolecular reaction itself at surface 12a.

Although a thin dome-shaped membrane 12 is shown in the figures, the invention is not so limited since other membrane shapes may be used in practice of the invention. A thin membrane, or region thereof, may have a convex shape relative to the substrate or a concave shape relative to substrate. The convex or concave shape may be made up of one or more arcuate surfaces and/or one or more linear surfaces such that a general convex or concave membrane shape is achieved. Furthermore, in other cases, the thin membrane does not have to be initially convex or concave as long as deflection of the membrane to a subsequent convex, concave or other shape can be achieved by induced membrane surface stress. For example, an initially flat membrane may possibly be used in the event that induced membrane surface stress as a result of interaction with a medium is effective to subsequently deflect the thin membrane to a convex, concave or other shape producing a deflection for sensing, actuation or other purposes. Also, a thicker membrane, or a membrane with regions of different thickness and/or hardness, may be deflected due to induced surface stress. Also, a thin membrane having a shape that is not symmetrical may be deflected by induced surface stress. In plan view, the thin membrane 12 may have a circular periphery, a polygonal periphery (e.g. a square periphery) or any other peripheral configuration.

Membrane Deflection Due To Internal Pressure:

For purposes of illustration and not limitation, the deflection of the thin membrane 12 can be evaluated by a simple analysis embodying the following conditions:
  Circular membrane
    Fixed boundaries
    Very thin membrane
and including the following assumptions:
the inflated portion of the thin membrane is a part of a sphere.
the radius of curvature of the dome-shaped membrane is much larger than membrane thickness.
the thin membrane cannot resist a bending moment.

There is an exact solution, but an approximate method will be used for simplicity in modeling the membrane with a surface stress later. The approximate solution will be compared with the exact solution here for justification.

In particular, in the event a plastic elastomeric membrane 12 is used in this invention, it is assumed that 1 μm thick membrane can be suspended with an initial 1 μm space or gap above substrate 10 where the space or gap dimension is measured at the peripheral edge of the shaped membrane 12. On the other hand, in the event an extremely small gap is used, it is assumed that 50 nm thick membrane 12 of hard material, such as silicon dioxide or silicon nitride, is suspended with 50 nm gap above substrate 10. These features of the thin membranes are all conservatively assumed for calculation, and can be reduced further if desired.

Figure 1:
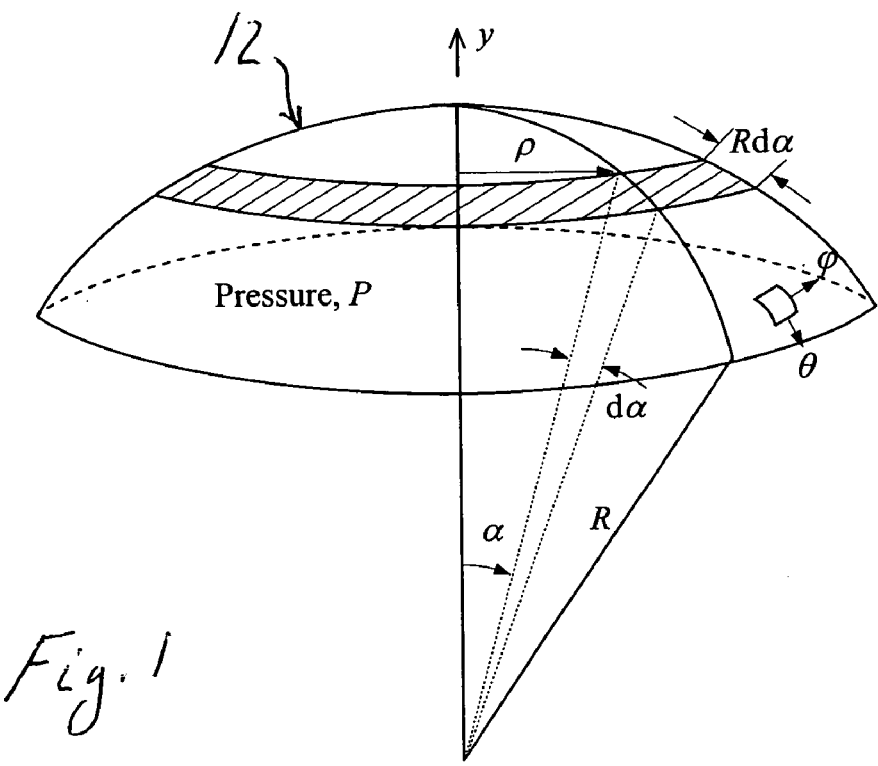
FIG. 1 is a schematic view of a thin elastomeric membrane for calculating membrane stress.

FIG. 1 shows the membrane deflected by internal gas pressure P (between the substrate and the inner membrane surface 12b). A force balance condition can be used for obtaining the relationship between the internal gas pressure P and the stress induced in the membrane. Note that the spherical coordinate is used with description in azimuth (θ) and tangential (φ) directions.

The y-direction force, sigma theta, by pressure on the entire area of the inflated membrane is expressed by:

$$F_p = \int_0^\theta P(2\pi R \sin\alpha) \cos\alpha R \, d\alpha$$
$$= \pi P R^2 \sin^2\theta$$

The y-direction force, sigma theta, by tensile stress in the membrane along the edge of the membrane is expressed by.

$$F_\sigma = \sigma_\theta \sin\theta t 2\pi R \sin\theta$$
$$= 2\pi R t \sigma_\theta \sin^2\theta$$

where R is the radius of curvature of the gas pressurized dome-shaped membrane. The magnitude of these two forces needs to be equal.

$$F_p = F_\sigma$$

Then $$\sigma_\theta = \frac{PR}{2t}$$

where t is the membrane thickness. In general, the stress in φ-direction is the same as the one in θ-direction.

$$\sigma_\varphi = \sigma_\theta = \frac{PR}{2t}$$

This has been verified in different approaches in the literature.

Membrane Strain:

The extension of the membrane without bending moment is assumed to be uniform throughout the entire area. Since there are two orthogonal stress components, the strain expressed in terms of stresses in these directions are:

$$\varepsilon_\theta = \frac{1}{E}(\sigma_\theta - v\sigma_\varphi) = \frac{PR}{2t}\frac{1-v}{E} = \frac{PR}{2tE^*}, \text{ where } E^* = \frac{E}{1-v}$$

where E is Young's modulus (Pa) of the membrane material and v is Poisson's ratio thereof. Note that the membrane strain can be expressed in terms of applied pressure.

The membrane strain can also be expressed in terms of geometry. The two expressions can be equated as follows. For example, from the membrane geometry shown in FIG. 3a and 3b, $$\varepsilon_\theta = \frac{l-l_o}{l}$$
$$= \frac{2R\theta - 2a}{2a}$$
$$= \frac{R\sin^{-1}\left(\frac{a}{R}\right) - a}{a}$$

From the stress-strain relation $$\varepsilon_\theta = \frac{PR}{2tE^*}$$

From the geometry of the inflated membrane, $$\sin\theta = \frac{a}{R}$$

Therefore, $$\sin^{-1}\left(\frac{a}{R}\right) = \frac{aP}{2tE^*} + \frac{a}{R}$$

or $$\frac{a}{R} = \sin\left[\frac{aP}{2tE^*} + \frac{a}{R}\right]$$

There is no closed form solution for this equation of the form:

$$x = \sin[y + x]$$

By solving this equation for R, we can obtain the deflection at the center of the membrane as a function of applied pressure.

$$d = R(1-\cos\theta) = R\left(1 - \frac{\sqrt{R^2 - a^2}}{R}\right)$$

The solution for the complete membrane profile can also be calculated since the profile is a part of a circle. Note that the membrane in this solution is assumed to be infinitesimally thin (e.g., like a soap bubble) so that it cannot transfer bending moment. Let us call this approach "membrane solution". A different solution is obtained if the membrane is assumed to transfer bending moment. An exact solution for the nonlinear bending can be obtained. This approach can be called a "shell solution".

Figure 4:
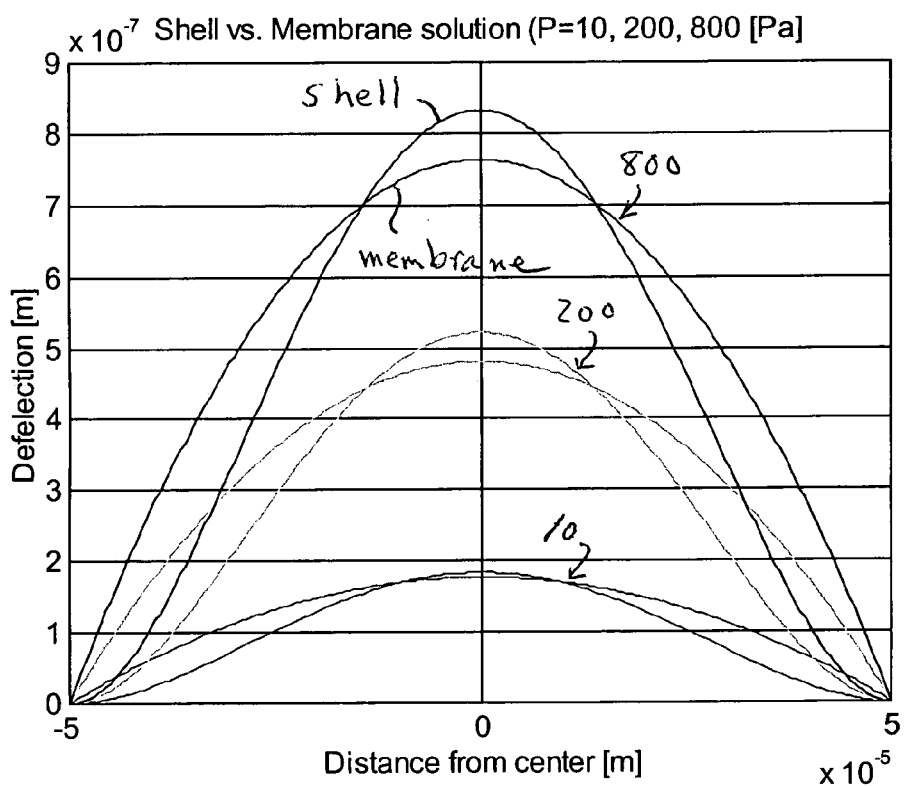
FIG. 4 is a graph showing the $SiO_2$ (silicon dioxide) membrane deflection when different pressures were applied. The graph was calculated by the shell method and the membrane assumption method.
Figure 5:
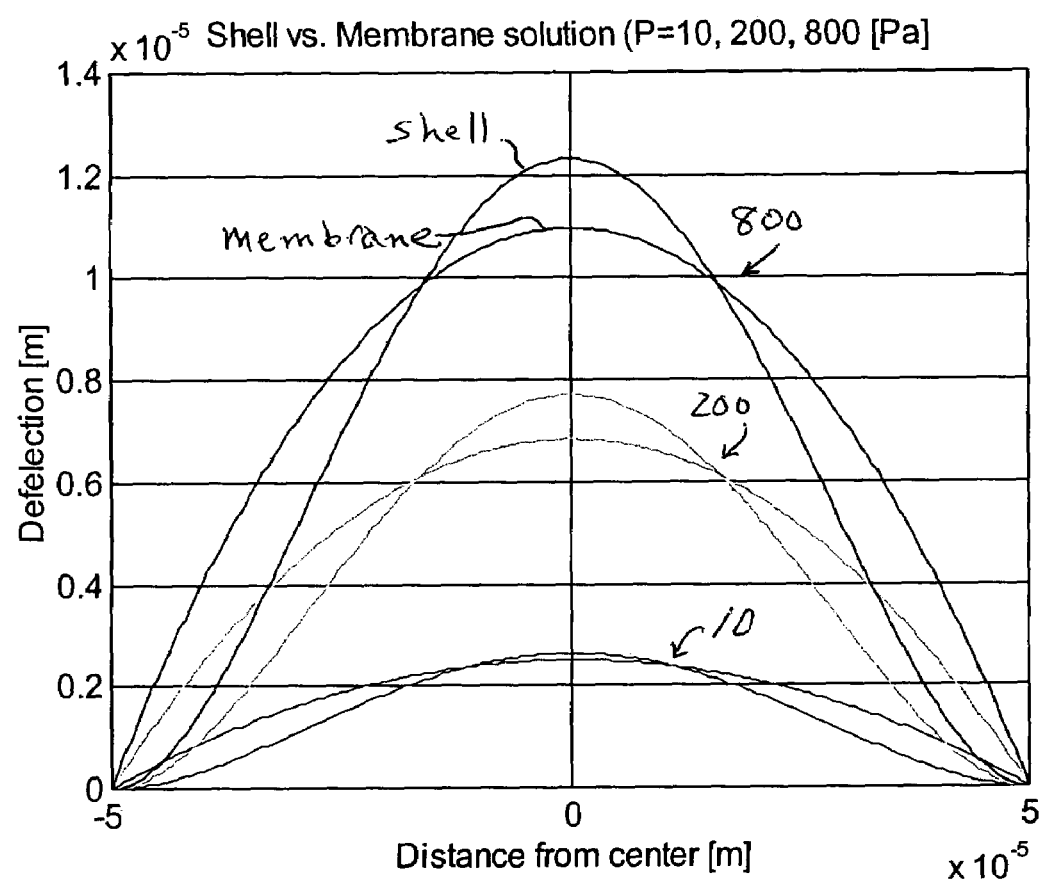
FIG. 5 is a graph showing PDMS (polydimethyl siloxane) membrane deflection when different pressures were applied. The graph was calculated by the shell method and the membrane assumption method.

FIGS. 4 and 5 show the comparison for the shell solution and the membrane solution with two different membrane materials, silicon dioxide and PDMS, respectively.

| Material Data (SiO$_2$) | |
|---|---|
| t = 0.05e−6 | [m], thickness of membrane |
| E = 70e9 | [Pa], Young's modulus |
| v = 0.17 | Poisson ratio |

| Material Data (PDMS) | |
|---|---|
| t = 1e−6 | [m], thickness of membrane |
| E = 750e3 | [Pa], Young's modulus |
| v = 0.5 | Poisson ratio |

As observed by the calculations shown in FIGS. 4 and 5, the difference by shell and membrane approach is reasonably small around 10% of the whole deflection. It is believed that the deflection change due to surface stress can be calculated by the simple membrane approach without much error.

Change of deflection due to surface stress, γ, is now described:

A chemical or biomolecular molecular reaction, or other interaction, on the surface 12a of the membrane 12 can induce surface stress there. The invention uses membrane deflection resulting from the induced surface stress caused by the chemical or biological reaction or other interaction on the surface 12a of the membrane. In the force diagram shown in FIG. 6, the surface stress is included. Analysis similar to the previous one can be performed with the effect of the surface stress considered.

Noting that the surface stress is a force per unit length, force balance equation can be written as follows.

$$F_{\sigma\gamma} = \sigma_\theta \sin\theta t 2\pi R\sin\theta + \gamma\sin\theta 2\pi R\sin\theta$$
$$= (\sigma_\theta t + \gamma)\sin\theta 2\pi R\sin^2\theta$$
$$F_p = F_{\sigma\gamma}$$
$$\pi R^2 P \sin^2\theta = (\sigma_\theta t + \gamma)\sin\theta 2\pi R\sin^2\theta$$
$$PR = 2(\sigma_\theta t + \gamma)$$
$$\sigma_\theta = \frac{1}{t}\left(\frac{PR}{2} - \gamma\right)$$

Figure 2:
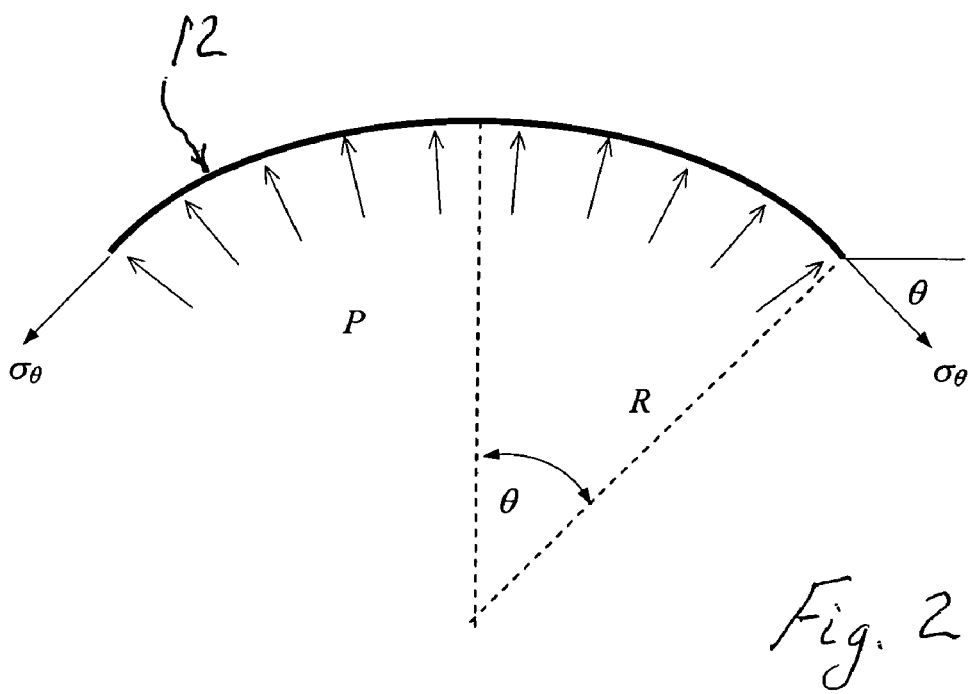
FIG. 2 is a schematic partial sectional view of a thin elastomeric membrane for calculating force balance of a gas pressurized or inflated membrane.
Figure 3A:
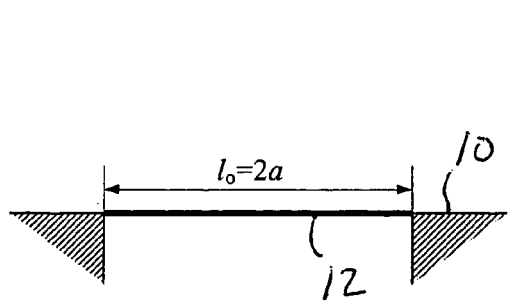
FIG. 3a is schematic partial sectional view of a thin elastomeric membrane before being inflated by gas pressure.
Figure 3B:
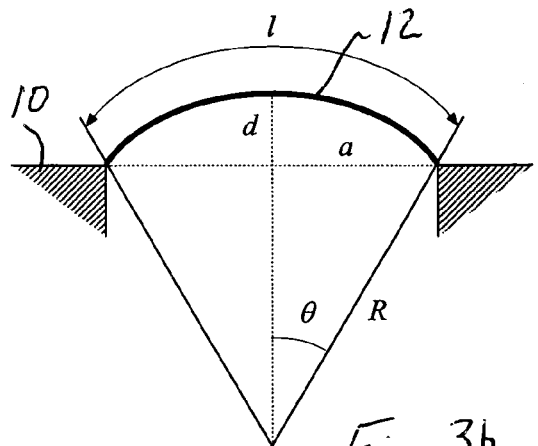
FIG. 3b is a similar view after the thin membrane is gas pressurized to inflate it to impart an arcuate dome shape.

Note that above equation is a modified form of the previous force balance equation described in connection with FIG. 2. If the surface stress is zero, this force balance equation becomes the previous equation.

The membrane strain is $$\varepsilon_\theta = \frac{1}{E}(\sigma_\theta - v\sigma_\varphi)$$
$$= \frac{1}{t}\left(\frac{PR}{2} - \gamma\right)\frac{1-v}{E}$$
$$= \frac{1}{E^*t}\left(\frac{PR}{2} - \gamma\right), \text{ where } E^* = \frac{E}{1-v}$$

This equals to the strain expression calculated previously.

$$\varepsilon_\theta = \frac{R\sin^{-1}\left(\frac{a}{R}\right) - a}{a} = \frac{1}{E^*t}\left(\frac{PR}{2} - \gamma\right)$$

Similar to the previous analysis again, this equation can be written in the following form.

$$\sin^{-1}\left(\frac{a}{R}\right) = \frac{a}{E^*t}\left(\frac{P}{2} - \frac{\gamma}{R}\right) + \frac{a}{R}$$

$$= \frac{aP}{2E^*t} + \frac{a}{R}\left(1 - \frac{\gamma}{E^*t}\right)$$

This expression is similar to the previous one except that there is a correction term β as shown below.

$$\sin^{-1}(x) = y + x\beta$$

or $$x = \sin[y + x\beta]$$

where beta is $(1-\gamma/E^*t)$ of the above equation. This equation can also be solved numerically.

| Case 1: PDMS membrane | |
| --- | --- |
| t = 1e−6 | [m], thickness of membrane |
| E = 750e3 | [Pa], Young's modulus |
| v = 0.5 | Poisson ratio |

Figure 7:
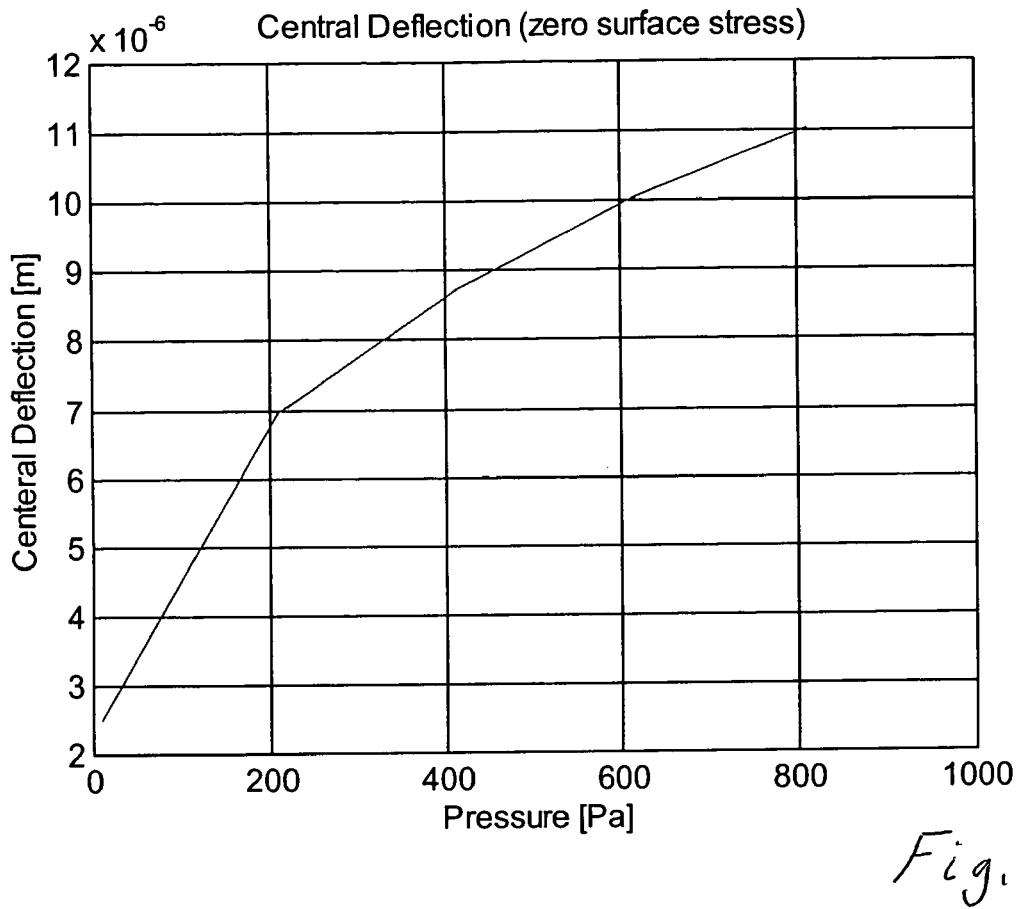
FIG. 7 is a graph showing central membrane deflection with zero surface stress when the pressure varies for a PDMS membrane, calculated by the membrane assumption method.
Figure 6:
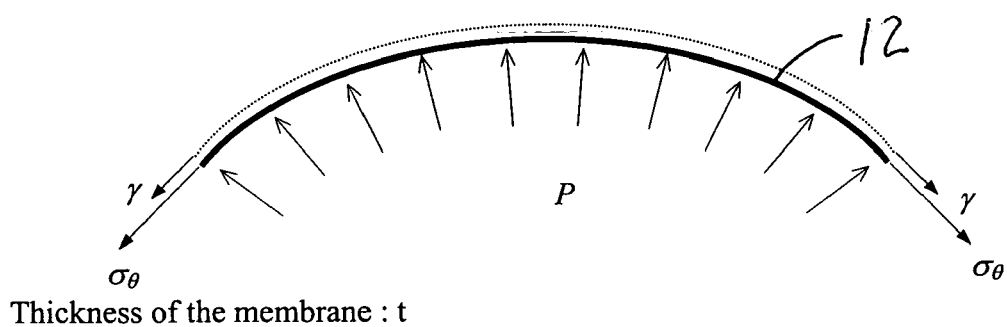
FIG. 6 is a schematic partial sectional view of a thin elastomeric membrane for calculating force balance of a gas pressurized membrane with surface stress considered.

FIG. 7 shows the deflection at the center of the membrane without the surface stress when the gas pressure between the substrate and the membrane varies. As the gas pressure varies from 10–800 Pa, the deflection changes from 2.5 μm –10 μm. This huge deflection is attributed to very small Young's modulus about five orders of magnitude smaller than that of silicon oxide. This low stiffness is one of the major advantages in obtaining very high sensitivity due to stress condition change such as surface stress in this invention.

Figure 8:
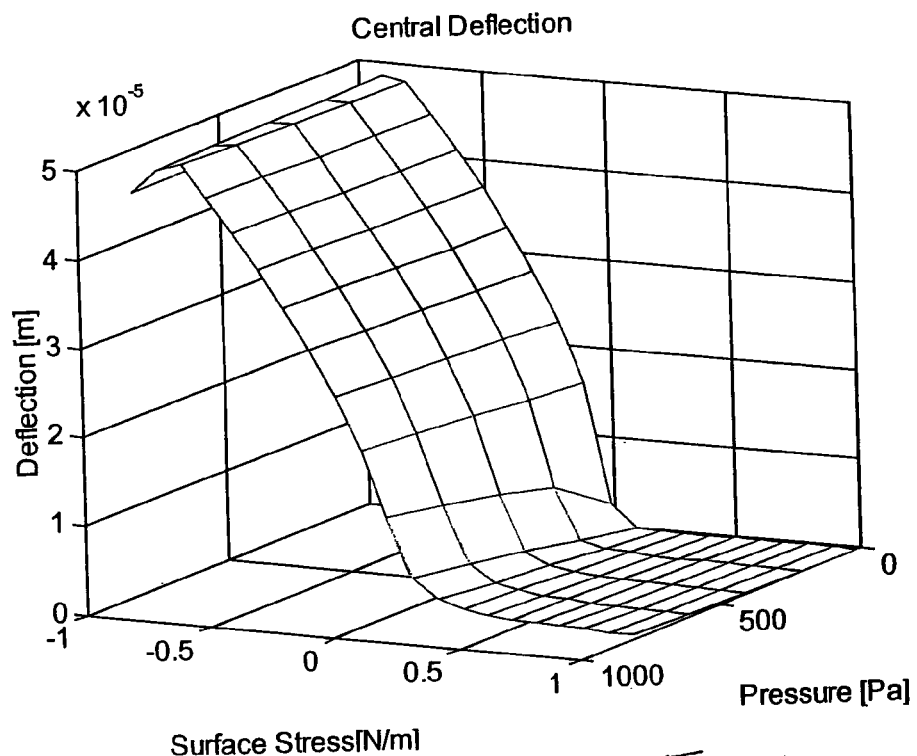
FIG. 8 is a graph showing central membrane-deflection with surface stress calculated by the membrane assumption method for a PDMS membrane.

FIG. 8 is the result of calculation for the membrane deflection considering the applied surface stress. The result is for the large variation in surface stress. It varied from −1 N/m (compression) to 1 N/m. The change in the deflection of membrane at the center is very large as shown in FIG. 8.

Figure 9A:
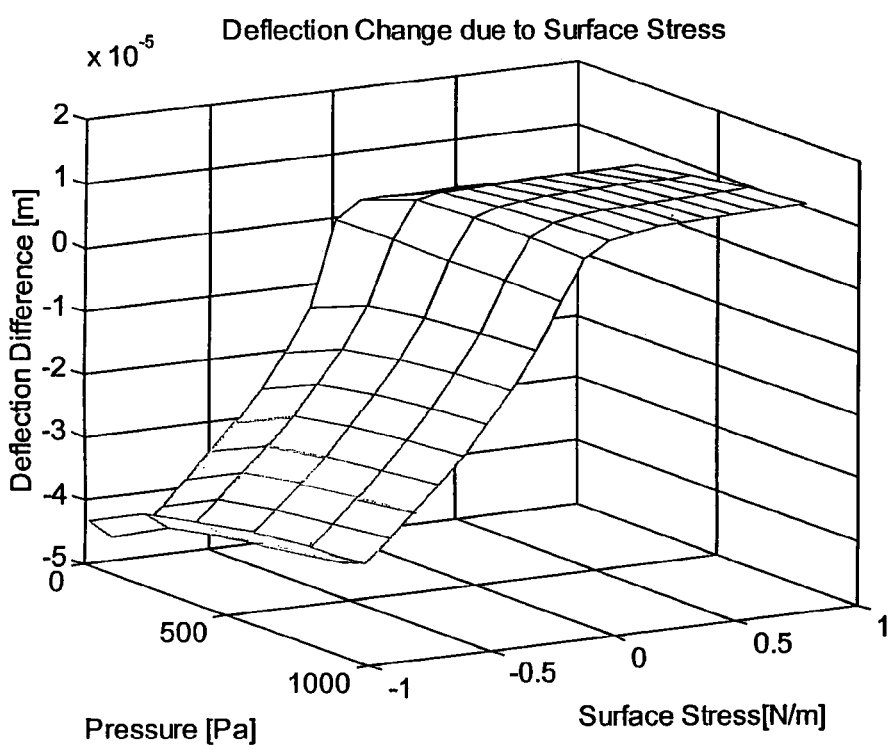
FIG. 9a is a graph showing central membrane deflection change by surface stress calculated by the membrane assumption method. [deflection without surface stress at certain pressure—deflection with surface stress at certain pressure for PDMS].
Figure 9B:
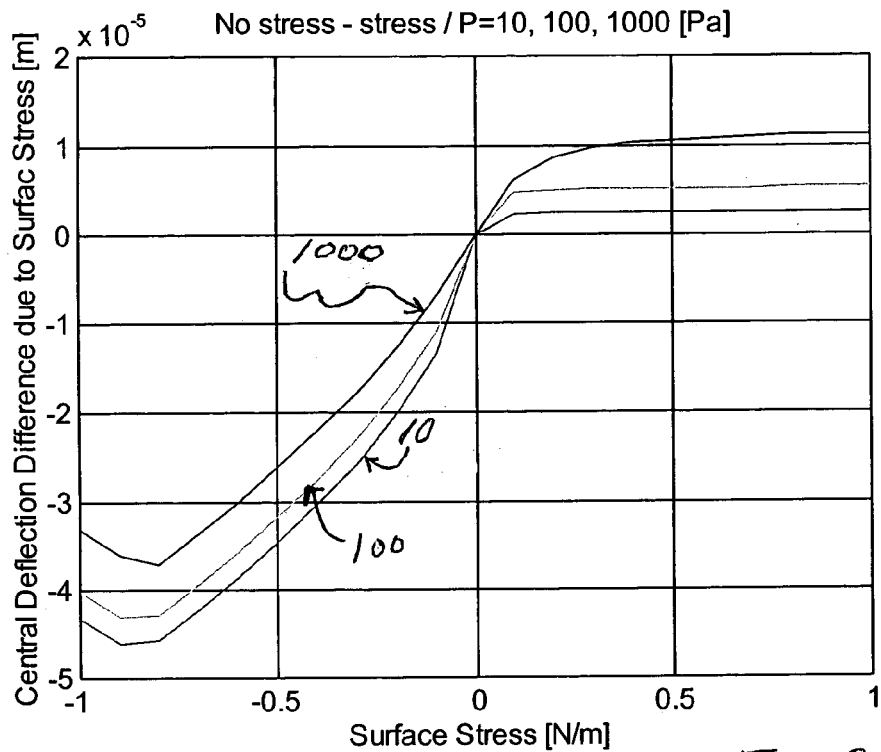
FIG. 9b is a two dimensional plot of the differences in central deflection due to different surface stress and pressures shown

FIGS. 9a and 9b show the difference in deflection at the center of the membrane due to the effect of surface stress. The z-axis value (deflection difference) is the difference between the membrane deflection without the surface stress (purely due to the internal gas pressure), and the membrane deflection for the given surface stress (due to internal gas pressure and applied surface stress). It is observed in FIG. 9 that the difference in deflection is very large in the range of 10 μm. It is also observed that the difference is more sensitive when the internal pressure is small, but becomes quickly saturated in this case. When high internal pressure is used, the difference becomes less sensitive to the surface stress variation, but covers more range without saturation.

When the surface stress is in tension, similar to the surface tension, the difference, i.e., subtracted value of the deflection with surface stress introduced from the deflection with zero surface stress, is positive. This means that the membrane deflection decreases as a result of the-applied-surface stress in tension. This result coincides with intuition, i.e., when the membrane surface is under the effect of shrinkage, it will deflect less with the same internal pressure between the substrate and the membrane. In contrast, when the surface stress is in compression, the membrane inflates more with the same amount of internal pressure.

Figure 10:
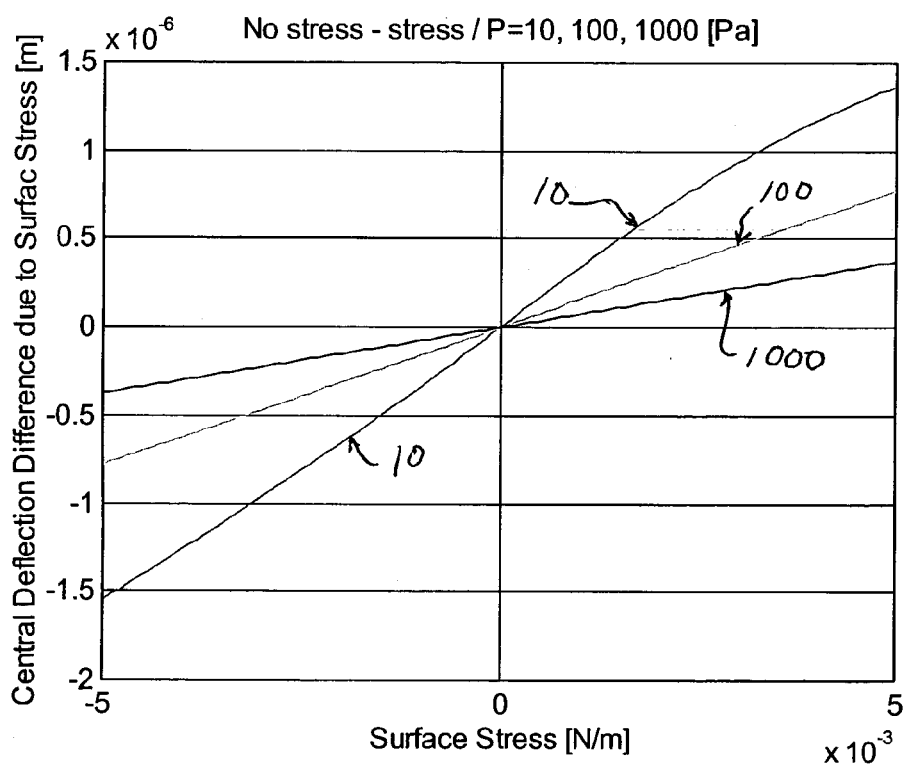
FIG. 10 is an exploded view of FIG. 9b in the medium stress range (−5 mN/m to 5 mN/m) at three different pressures.

FIG. 10 is an exploded view of the FIG. 9(b) in the medium range variation of the surface stress−−5 mN/m–5 mN/m. As shown in FIG. 10, the amount of the deflection change (∼1.5 μm) is still reasonably large and measurable. Also, the relationship between the deflection difference and the applied surface stress is quite linear.

Figure 11:
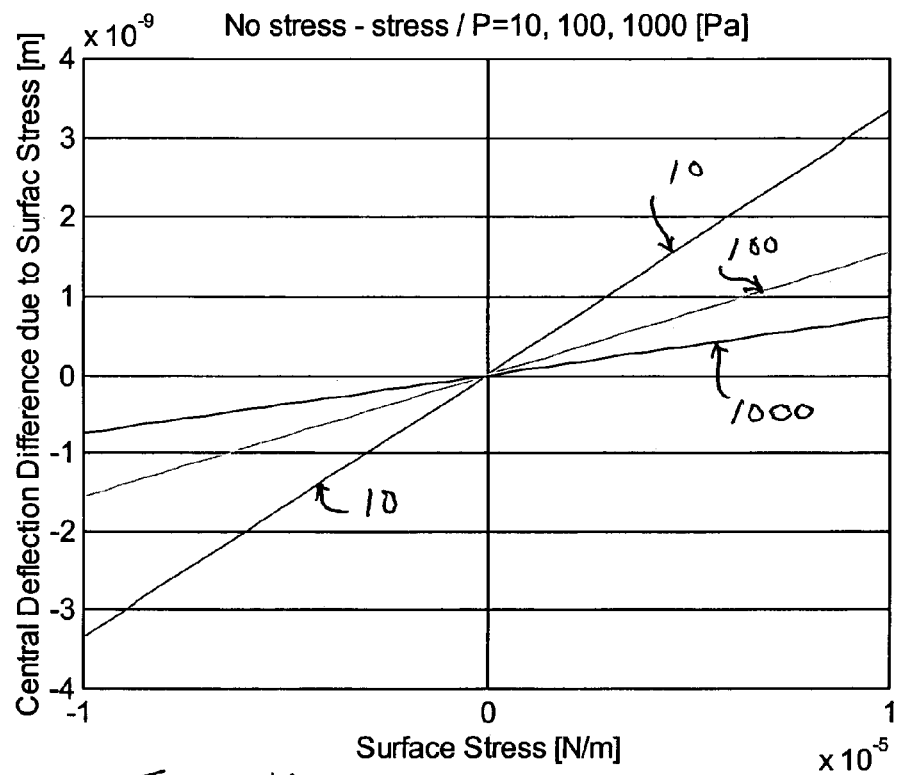
FIG. 11 is an exploded view of FIG. 9b in the stress range (−0.01 mN/m to 0.01 mN/m) at three different pressures.
Figure 12:
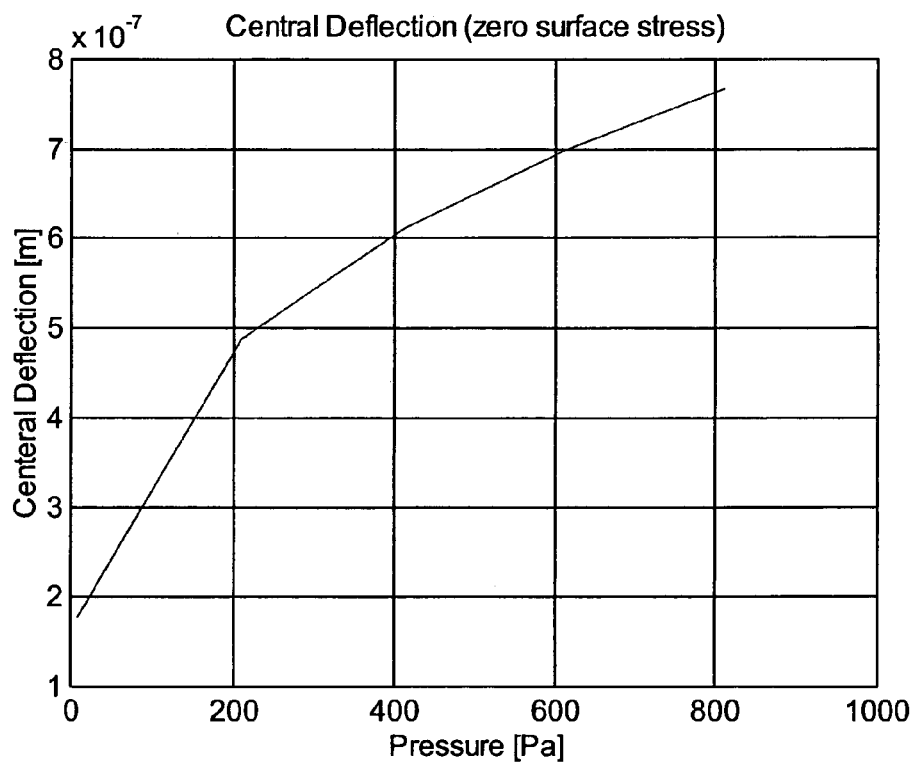
FIG. 12 is a graph showing central membrane deflection with zero surface stress calculated by the membrane assumption method for a $SiO_2$ membrane comprising a hard ceramic such as silicon dioxide or silicon nitride.
Figure 13:
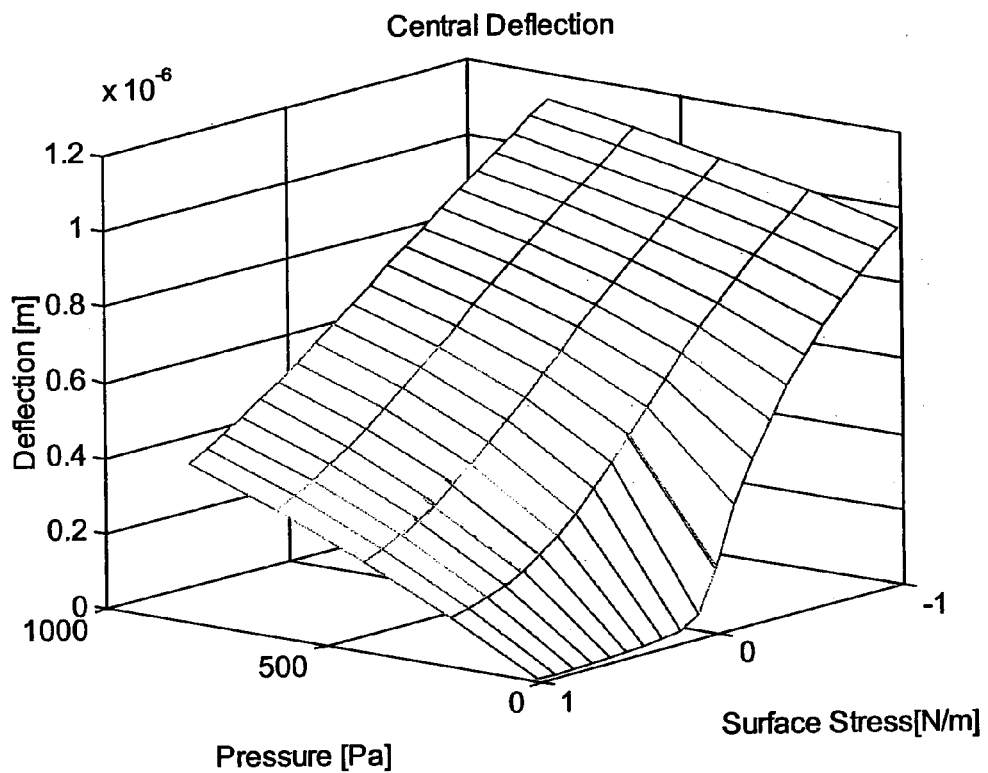
FIG. 13 is a graph showing central membrane deflection with surface stress calculated by the membrane assumption method for a $SiO_2$ membrane.
Figure 14A:
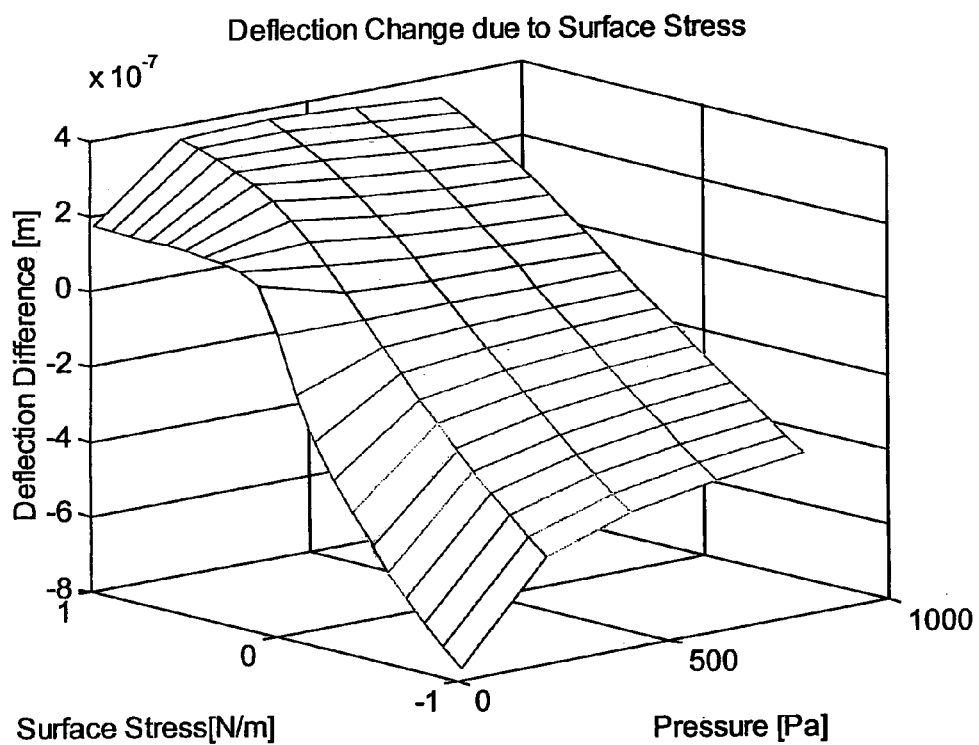
FIG. 14a is a graph showing central membrane deflection change by surface stress calculated by the membrane assumption method. [deflection without surface stress at certain pressure—deflection With surface stress at certain pressure for $SiO_2$].
Figure 14B:
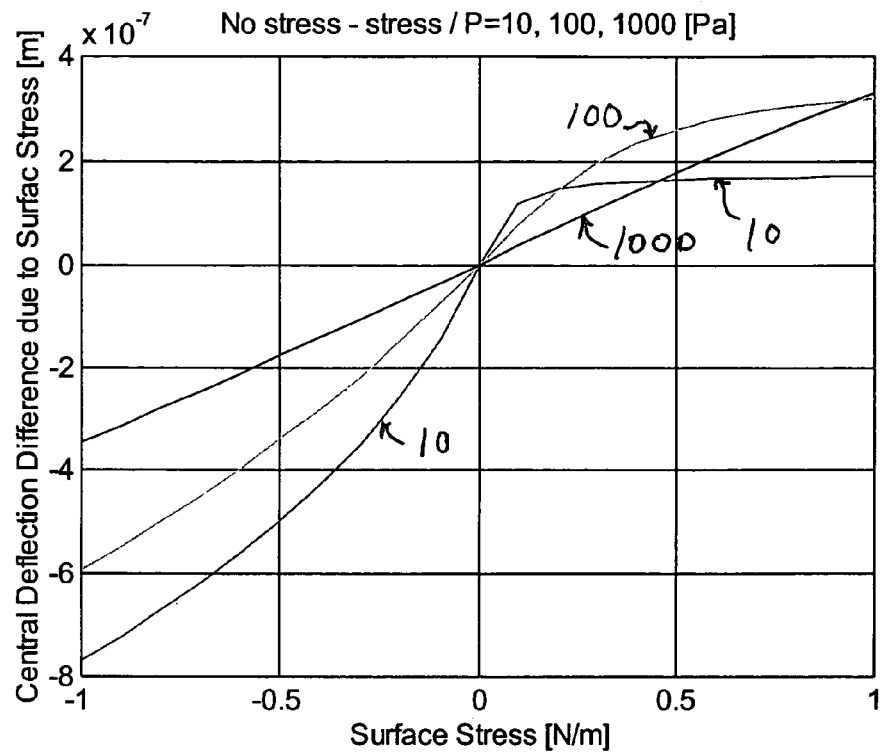
FIG. 14b is a two dimensional plot of the differences in central deflection due to different surface stress and pressures shown
Figure 15:
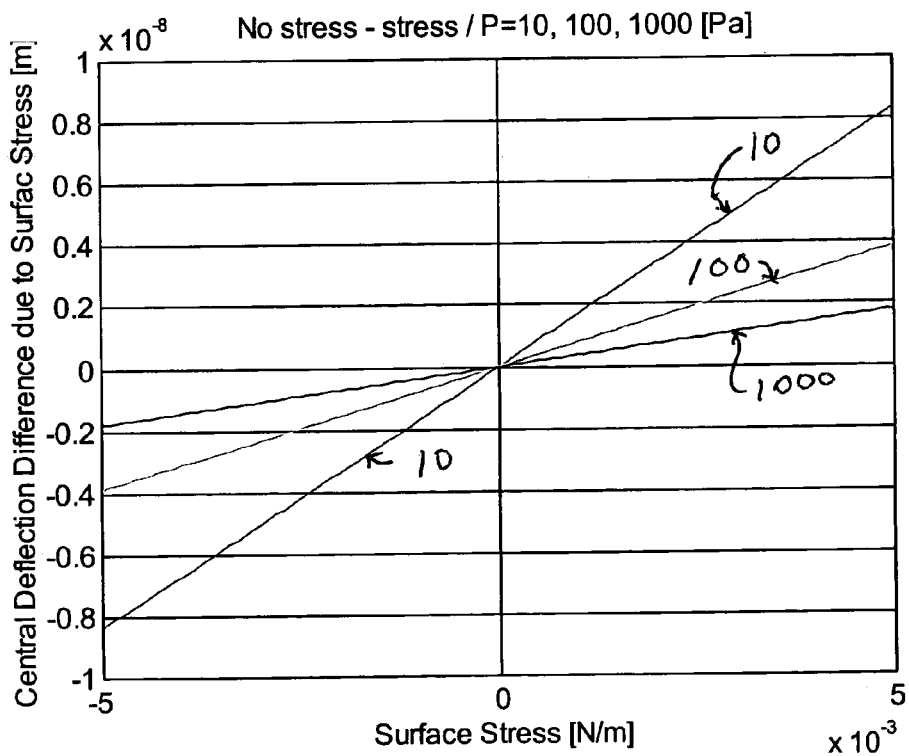
FIG. 15 is an exploded view of FIG. 14b in the medium stress range (−5 mN/m to 5 mN/m) at three different pressures.
Figure 16:
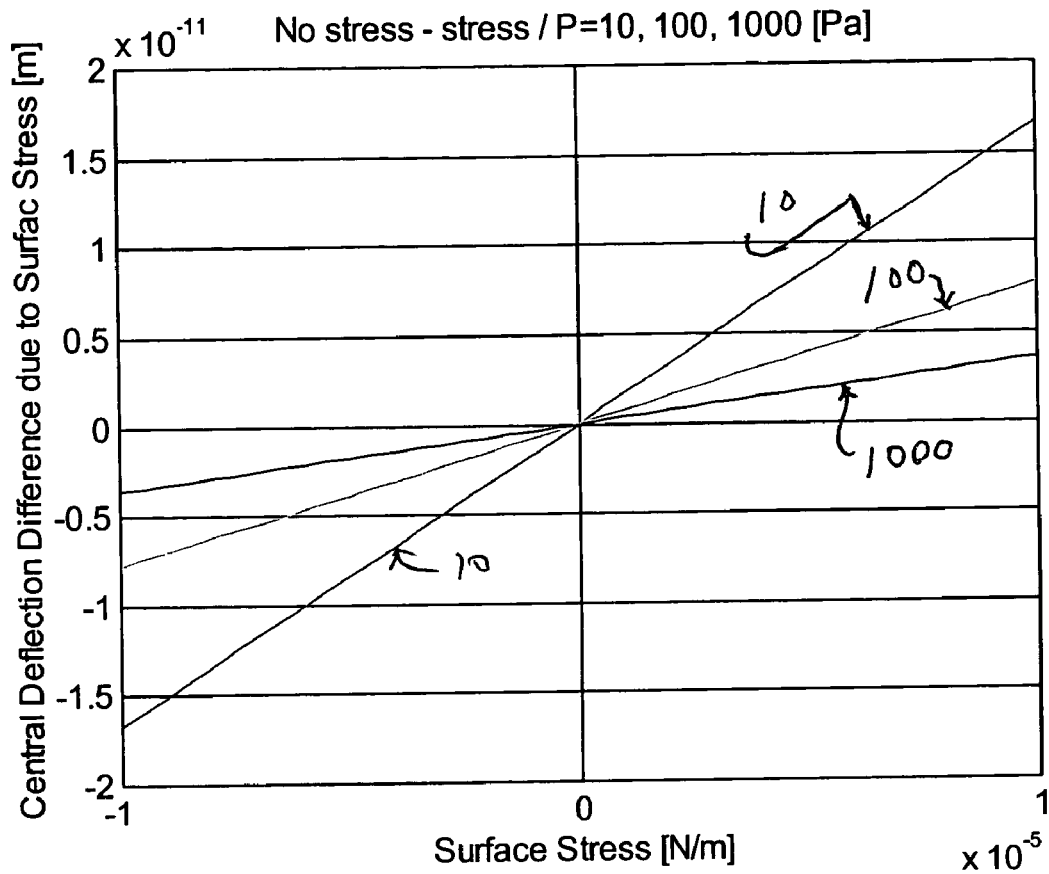
FIG. 16 is an exploded view of FIG. 14b in the stress range (−0.01 mN/m to 0.01 mN/m) at three different pressures.
Figure 17:
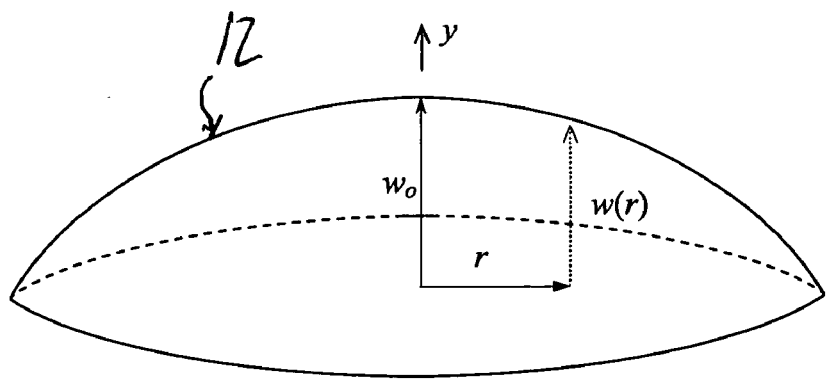
FIG. 17 is a schematic view of a deflected thin membrane and coordinate system to describe membrane deflection.

FIG. 11 is highly exploded view for the amount of surface stress ranging from −0.01mN/m to 0.01 mN/m. The range of deflection for these values is approximately 1 to approximately 3 nm. Later it will be shown that this variation can be reasonably well detected with capacitive measurement. The deflection difference is linear.

| Case II: Silicon dioxide (SiO$_2$) membrane | |
| --- | --- |
| t = 0.05e−6 | [m], thickness of membrane |
| E = 70e9 | [Pa], Young's modulus |
| v = 0.17 | Poisson ratio |

FIGS. 12–16 show the calculated results for the deflection at the center of a membrane, made of a hard ceramic material, such as silicon dioxide (or silicon nitride), with the same conditions given for FIGS. 7–11. It is observed that the linearity is better for the silicon dioxide membrane, but the difference in deflection is much less than that of the PDMS membrane. For example, the deflection difference for the surface stress of 0.01 m N/m is only 8pm for silicon dioxide membrane, while it is 1.5 nm for the same amount of surface stress; i.e., an approximately 100 times difference. Nevertheless this small difference can be sensed by very small gap capacitance.

Capacitance Variation Due To Membrane Inflation

The deflection as a result of inflation-of thin membrane 12 can be measured by capacitance between electrodes associated with the membrane 12 and the substrate 10. There are again two cases with different materials. The thickness and material data are shown previously.

Case I: PDMS Membrane

Initial gap size before membrane deflection: 1 μm measured at the peripheral edges or center of the membrane when the membrane is flat. This gap size between the PDMS membrane and the substrate is assumed for ease of fabrication with PDMS thin membrane, but this value can be further varied for higher sensitivity. This analysis therefore is conservative in this sense. As for the electrodes, a very thin metal layer electrode 14 can be deposited on the underside (or top side depending on membrane thickness) of the PDMS membrane, FIGS. 20b and 33b, or alternatively the elastomer membrane itself can be made to be conductive and also function as an electrode. A second electrode 16 can be provided on the substrate surface or a distance below the surface of the substrate 10 beneath the gap between the membrane and the substrate as shown in FIG. 33b. A capacitance measuring device C, such as a high precision capacitance meter, can be connected by lead wires shown schematically between the electrodes, FIG. 33b, to measure the capacitance between the electrodes 14 and 16.

Initial capacitance (no internal pressure, no surface stress) expressed as:

$$C = \frac{\varepsilon_0 A}{d} = \frac{\varepsilon_0 \pi a^2}{d}$$

$\varepsilon_0 = 8.854 \times 10^{-12}$ F/m: dielectric coefficient of vacuum or air
$a = 50$ μm: radius of circular membrane
$d = 1$ μm: initial gap distance of flat membrane Calculated capacitance, C=69.5 fF This capacitance is a reasonable number for the capacitive measurement as an initial capacitance before variation.

Variation Of Capacitance Due To Membrane Inflation:

As the thin membrane 12 deflects due to applied internal gas pressure P and surface stress, the capacitance also is varying. In this analysis the deflection at the center of the membrane is calculated using membrane theory as shown previously. The capacitance of the deflected membrane can be calculated assuming the deflection profile from a shell solution as follows:

Assume deflection profile:

$$w(r) = w_o \left[1 - \left(\frac{r}{a}\right)^2\right]^2$$

where $w_o$ is deflection at the center.

Capacitance:

$$C = \int_A \frac{\varepsilon_o}{d + w(r)} dA$$

$$= \int_0^{2\pi} \int_0^a \frac{\varepsilon_o}{d + w_o\left[1 - \left(\frac{r}{a}\right)^2\right]^2} r\, dr\, d\theta$$

$$= 2\pi\varepsilon_o \int_0^a \int_0^a \frac{r}{d + w_o\left[1 - \left(\frac{r}{a}\right)^2\right]^2} dr$$

$$= 2\pi\varepsilon_o \frac{1}{2} a^2 \tan^{-1}\left[\frac{1}{2} \frac{2w_o r^2 - 2w_o a^2}{a^2 \sqrt{dw_o}}\right]_{r=0}^{r=a}$$

$$= \frac{\pi\varepsilon_o a^2}{\sqrt{dw_o}} \tan^{-1}\sqrt{\frac{w_o}{d}}$$

Figure 18:
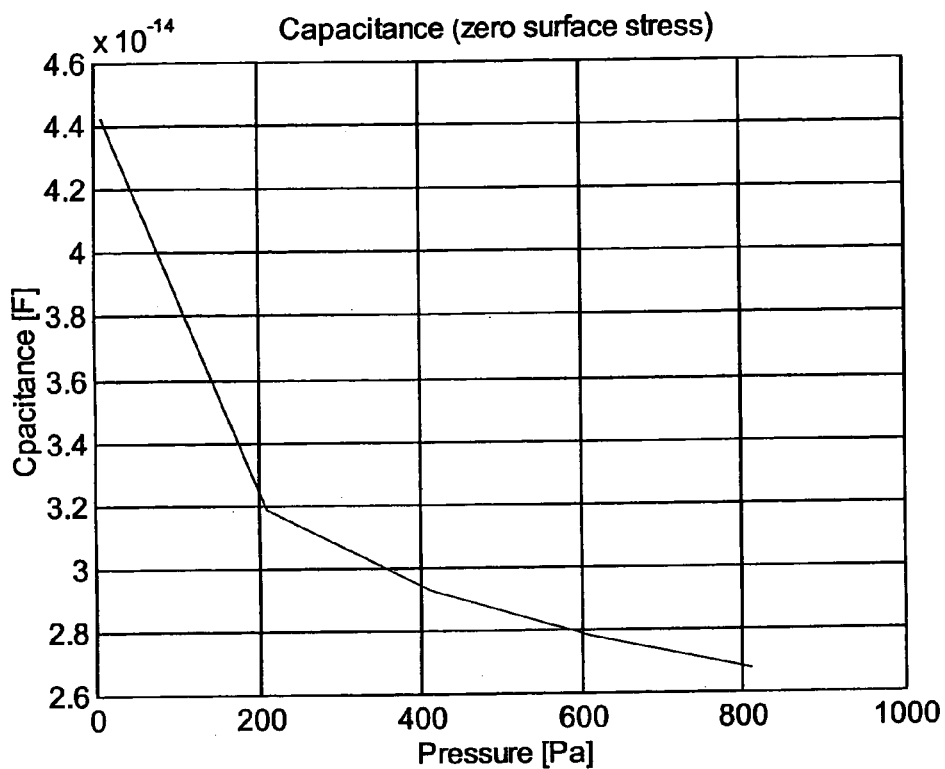
FIG. 18 is a graph of calculated capacitance between the substrate and the PDMS membrane versus gas pressure without surface stress.
Figure 19:
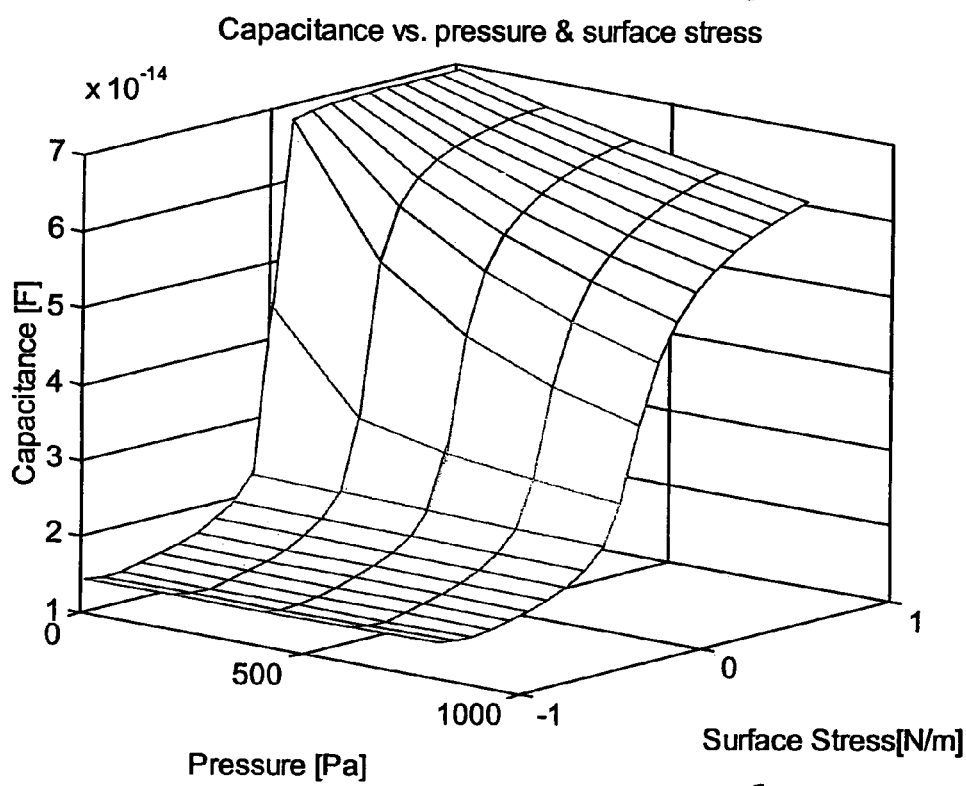
FIG. 19 is a graph of calculated capacitance between the substrate and the PDMS membrane versus gas pressure with surface stress.

The calculated deflection at the center, d is inserted in the above formula. FIG. 18 shows the plot of the calculated capacitance due internal gas pressure variation with zero surface stress. FIG. 19 shows the capacitance due to internal gas pressure and applied surface stress. The range of the capacitance ~10 fF is reasonable a value for the initial capacitance for measurement.

Capacitance Measurement Principle:

The following underlines the measurement principle
Inflated membrane
Differential capacitance→rejects external disturbance, rejects thermal drift
membrane with chemical binding site coated
membrane without chemical binding site
Multiple area to increase sensitivity
Differential pressure for different sensing range Inflating of a thin elastomeric membrane 12 to impart a dome shape is used in the embodiment of the invention of FIG. 20a. Without inflation of the thin elastomeric membrane 12 in this embodiment to impart the dome shape to the membrane, the surface stress cannot be observed. For example, a flat thin elastomeric membrane without pressure does not deflect even though it is affected by surface stress in tension. A flat elastomeric membrane without pressure will just buckle if there is surface stress in compression. By inflating the thin membrane 12 to a dome shape in FIG. 20a and observing the difference in deflection, the effect of surface stress can be observed in a stable manner. Although a thin inflated dome-shaped membrane 12 is described in this embodiment, the invention is not so limited since other membrane shapes may be used in practice of the invention as described above. Moreover, the thin membrane may be fabricated to have a self-supporting dome shape in that there is no need to inflate the membrane by the internal gas pressure to impart and maintain the dome shape to the thin membrane. A method for fabricating a self-supporting dome shaped membrane is described below.

Pursuant to a particular sensor aspect of the invention, the sensor 5 also comprises a dummy membrane 22, that does not have any chemical binding sites, fabricated and located adjacent to the functional membrane 12, that is coated with chemical binding sites, as illustrated in FIGS. 20a and 20b. The difference in capacitance $C_r$ shown schematically associated with electrodes of the functional membrane 12 and the substrate 10 and the capacitance $C_o$ shown schematically associated with the non-functional, dummy membrane 22 and the substrate 10 is then measured. This differential measurement is advantageous to avoid external disturbance and thermal drift effects. The overall sensitivity of the sensor can be effectively increased by multiple numbers of the individual capacitance units.

In practice of the invention, the sensed capacitance signal can be saturated due to high surface stress. Different internal membrane pressure P can be used for different sensing range as a result. For example, higher internal pressure (such as 1 kPa) will be used for measuring larger surface stress. Sensitivity will be lower in this case, but the saturation of the measurement signal will not occur. Lower internal pressure (such as 10–100 Pa) will be used for very small surface stress. Sensitivity will be very large in this case. Saturation will occur at lower concentration or surface stress. This mode can also be used for yes/no detection of chemical and/or biomolecular binding or reaction with the reaction sites on membrane surface 12a with very high sensitivity.

Figure 21:
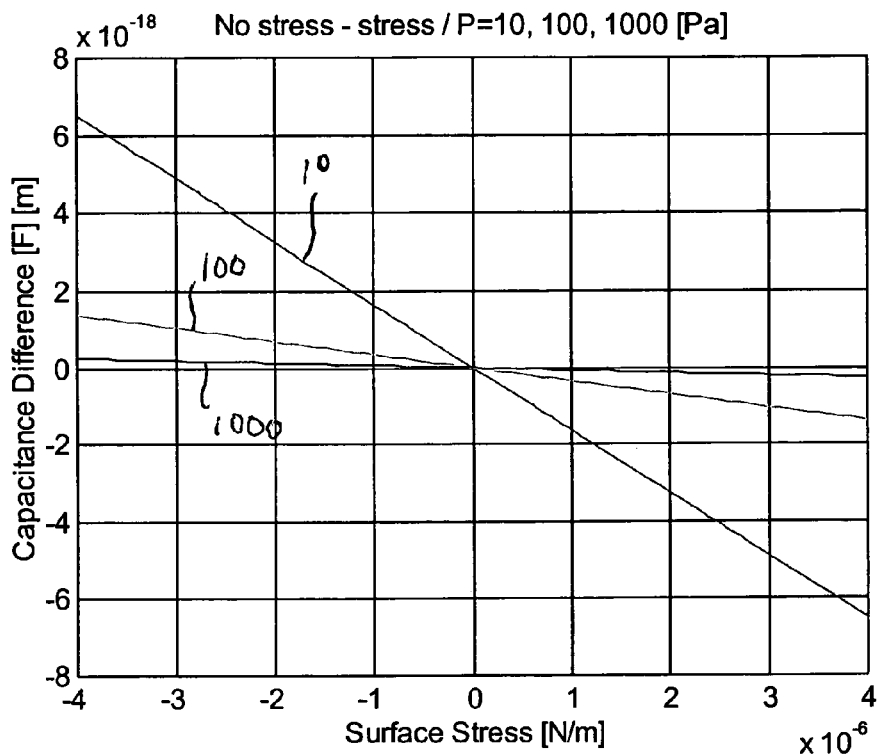
FIGS. 21 and 22 are graphs of capacitance differences between electrodes of the substrate and the PDMS membrane versus gas pressure with small and medium surface stress.

FIG. 21 shows the capacitance difference due to small values of surface stress. It is observed that the signal is highly linear. An accepted detection limit of the capacitance variation is $5 \times 10^{-15}$ F. This number for the detection limit from FIG. 21 corresponds to the surface stress of ~3 μN/m. The invention can detect approximately 3 μN/m of surface stress and this corresponds to the surface stress of less than 100 pM. If a multiple sensing units in an 10×10 array are used, the detection limit would be less than 1 pM. This implies that this invention can have similar detection limit to that of optical detection. In contrast, current micro-cantilever technology can detect ~5 mN/m of surface stress that corresponds to 100 nM concentration of molecules in an analyte.

Figure 22:
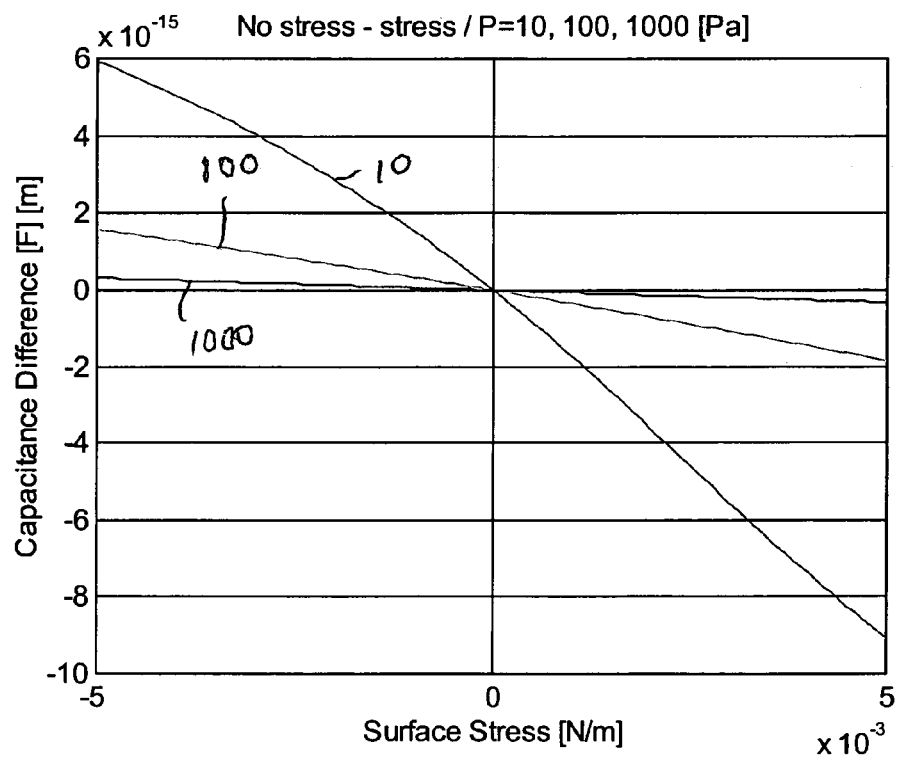
Figure 23:
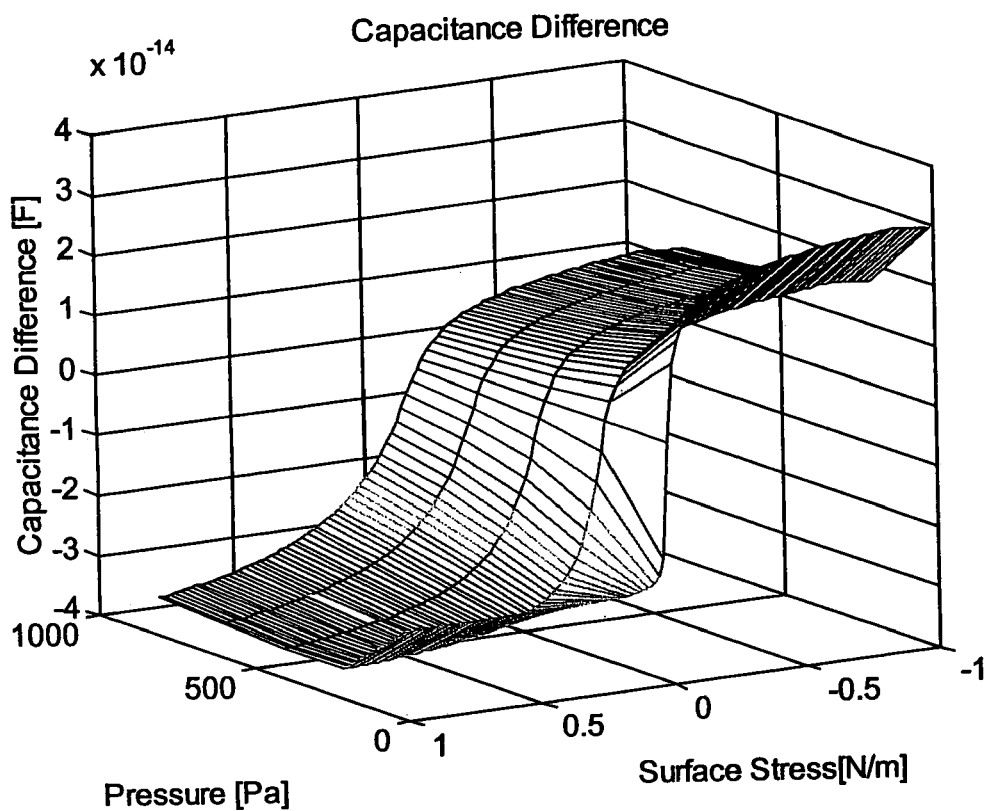
FIG. 23 is a graph of capacitance differences due to surface stress with different gas pressure.
Figure 24:
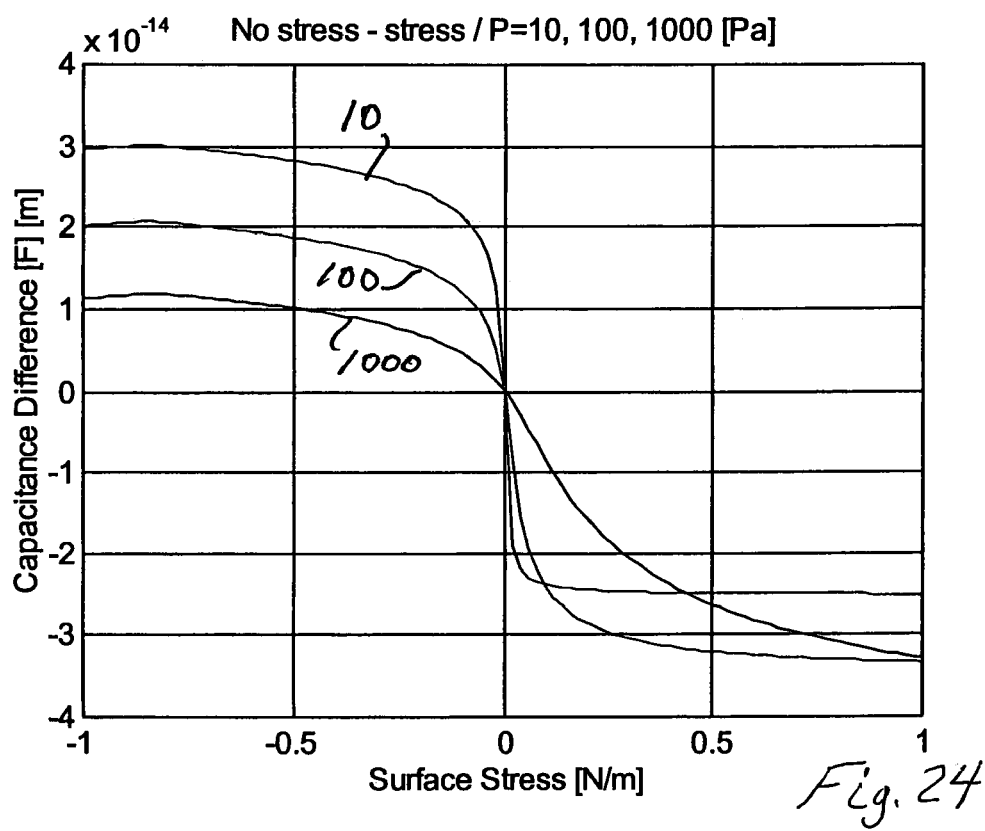
FIG. 24 is a graph of capacitance differences due to surface stress with large signal response (PDMS).
Figure 25:
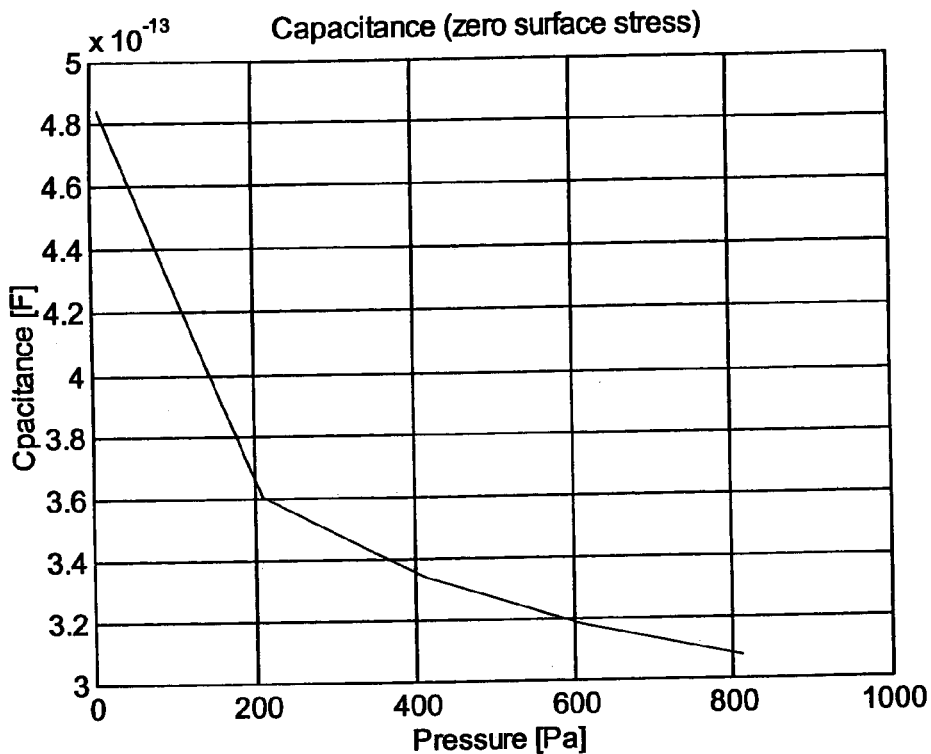
FIG. 25 is a graph of calculated capacitance between electrodes of the substrate and the $SiO_2$ membrane versus gas pressure without surface stress.
Figure 26:
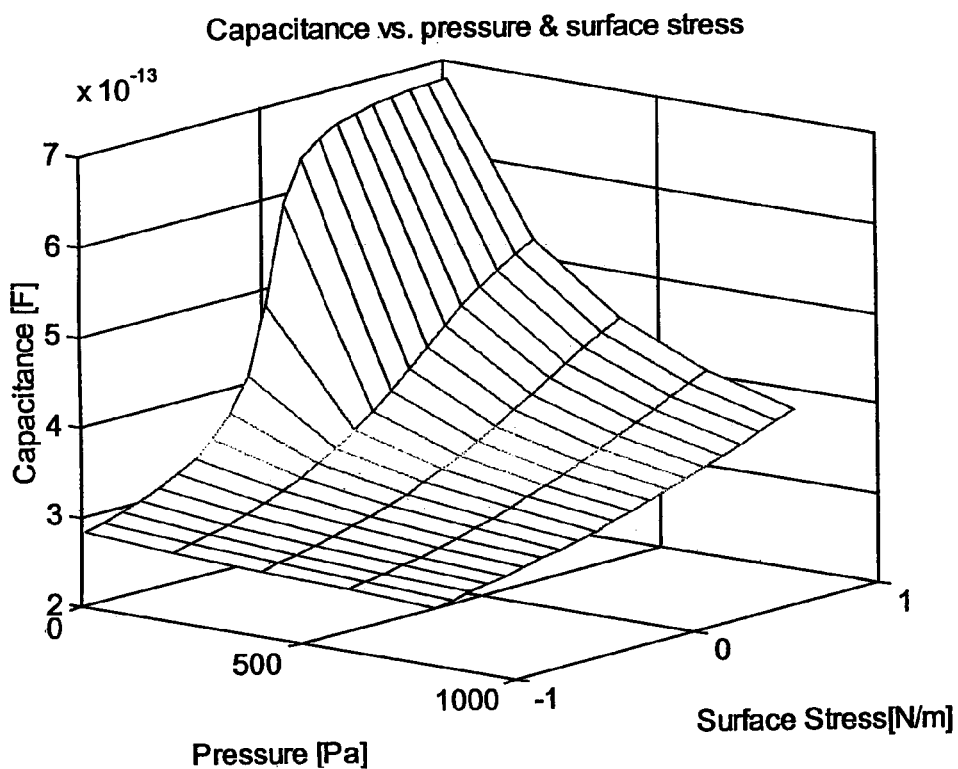
FIG. 26 is a graph of calculated capacitance between electrodes of the substrate and the $SiO_2$ membrane versus gas pressure with surface stress.
Figure 27:
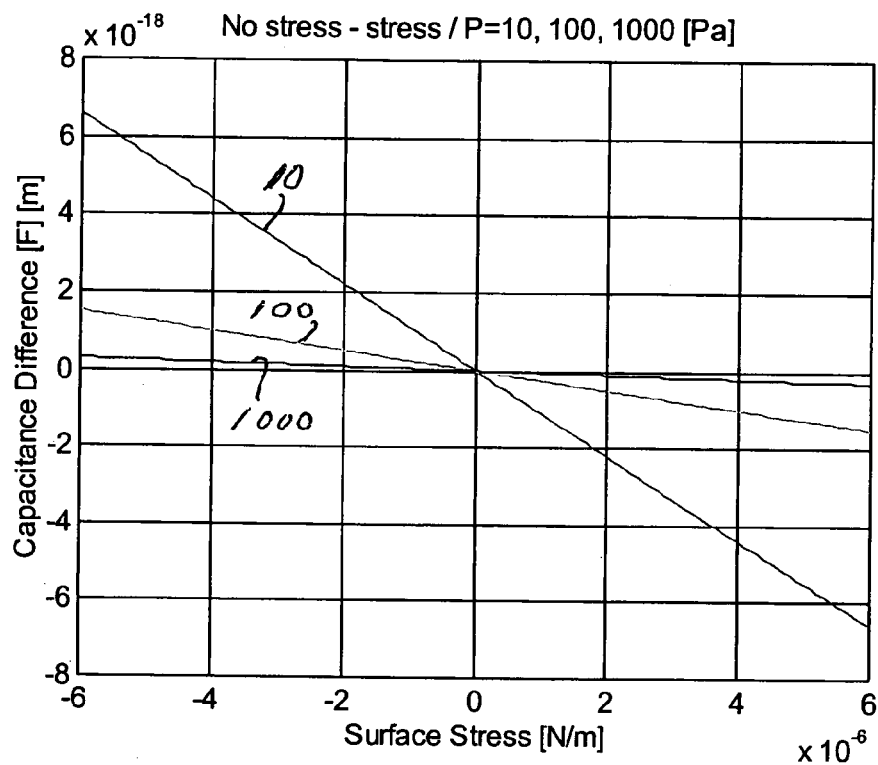
FIGS. 27 and 28 are graphs of capacitance differences due to surface stress with small and medium signal response ($SiO_2$).
Figure 28:
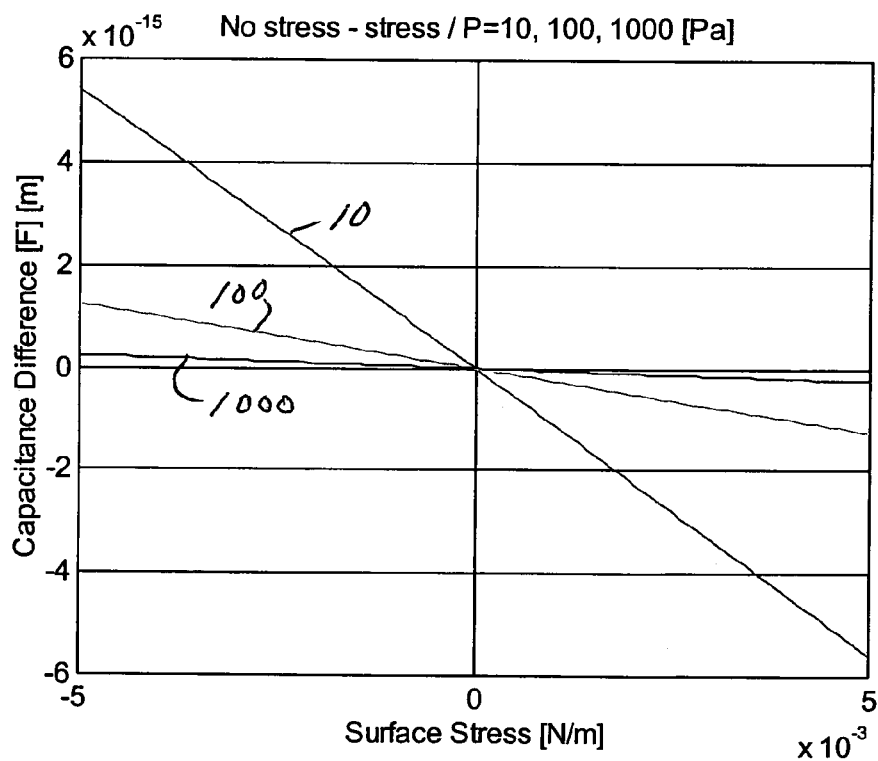
Figure 29:
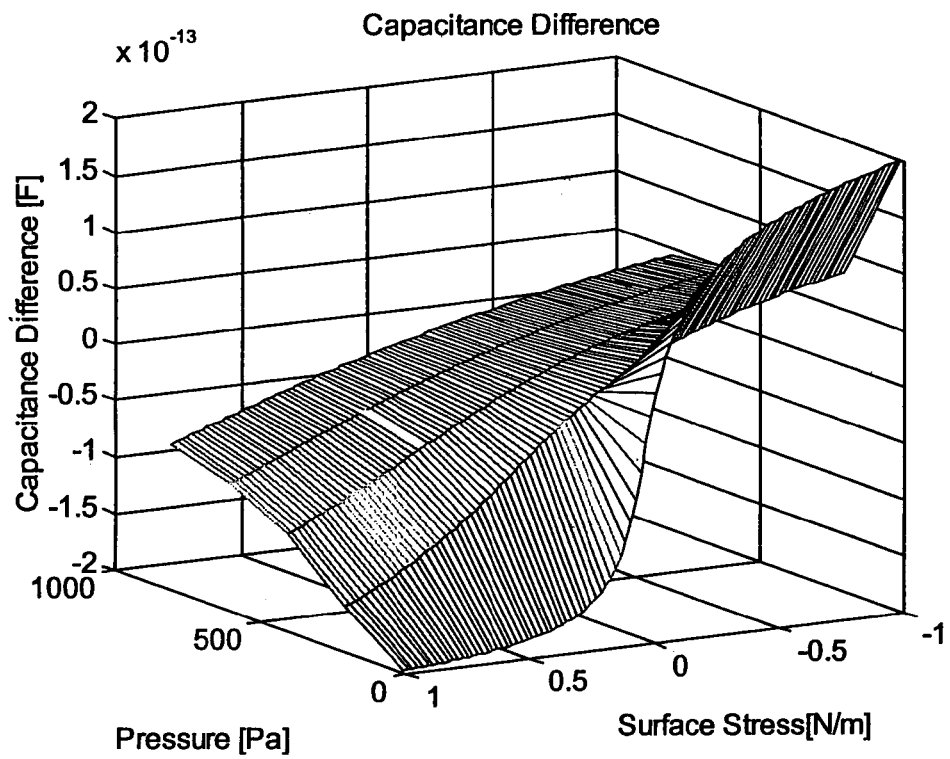
FIG. 29 is a graphs of capacitance difference detection with different gas pressures.
Figure 30:
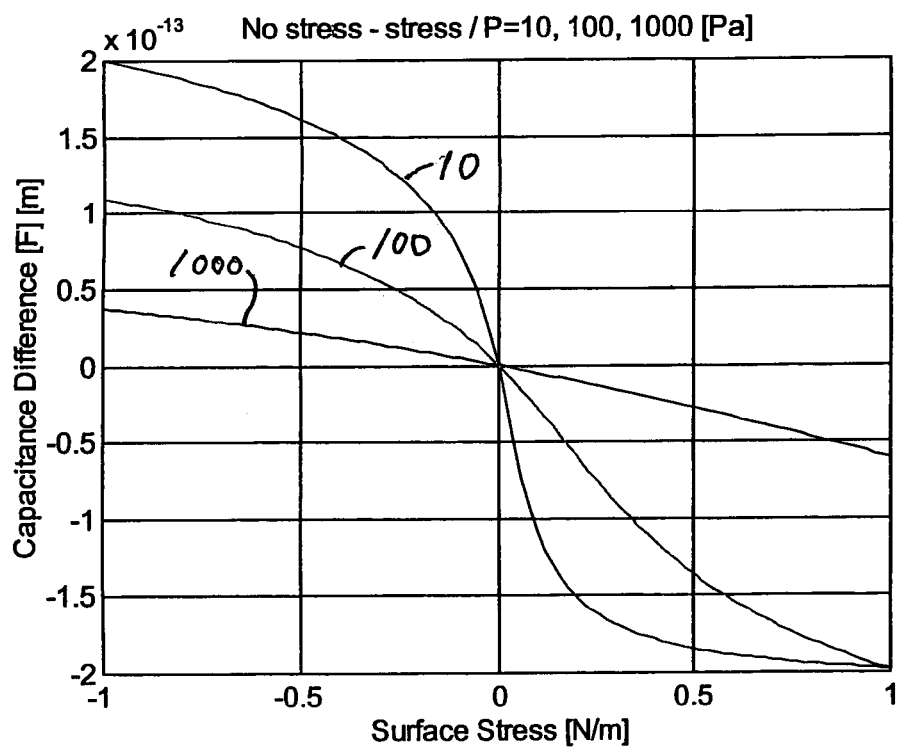
FIG. 30 is a graph of capacitance differences due to surface stress with large signal response ($SiO_2$)

FIG. 22 shows the capacitance signal for the medium range of surface stress, while FIGS. 23 and 24 show the signal responses for the large variation of surface stress. If the internal membrane pressure is low, very high sensitivity is obtained, but the signal is quickly saturated. By using higher internal membrane pressure such as 1 kPa, this large range of signal, e.g., 1 N/m, can be detected. Very large dynamic range is obtained due to this multiple mode operation. The low-pressure mode operation can also be used for very high sensitive yes/no detection of a chemical and/or biomolecular binding or reaction at reaction sites on membrane surface 12a.

Case II: Silicon Dioxide

Gap size: 0.1 µm

The thickness of the membrane 12 is 0.05 µm and the physical gap size between the substrate and the membrane is 0.05 µm at the peripheral edges or center of the membrane when the membrane is flat. A very thin metal electrode is deposited on the top (or underside) of the silicon dioxide film so that the "electrical" gap for capacitance will be 0.1 µm at the peripheral edges or center of the flat membrane. The relative dielectric constant of silicon dioxide, approximately 4, is not considered here. The result below is thus conservative.

FIGS. 25 to 30 show results for silicon dioxide membrane of the type described. The overall performance is very similar to that of the PDMS membrane. Even though the silicon dioxide is a hard ceramic material that has much larger stiffness than PDMS, the gap size and the membrane thickness that can be created are also small, resulting in comparable performance. A silicon dioxide device may have better performance in terms of the linearity and symmetry of the sensed capacitance signals.

Although the change of capacitance has been described above with respect to detection of membrane deflection, the invention is not so limited since other detection techniques may be used. For example, optical detection of membrane deflection can be used using an inteferometry type optical detector. Moreover, piezoelectric detection can be used wherein a piezoelectric layer is applied on the membrane surface 12a or 12b to measure membrane deflection.

Multiple Array Detection:

Use of array of sensors pursuant to the invention provides the following advantages to the invention.
1) Increased sensitivity
2) Multiple detection Increased Sensitivity:

For example, referring to FIG. 31, if there are n×n detection units (sensors), the overall sensitivity will increase by n×n times. When sensors 5 in a 10×10 array having reaction agent-coated and uncoated thin membranes 12 and having a 100 µm membrane diameter are used, the overall size of the area is approximately 1 $mm^2$ which is still small. As described previously, a sub-pico molar detection is possible in this case. The sensors 5 can be provided on the same substrate or on different substrates.

Multiple Detection:

Referring to FIG. 32, multiple detection of multiple chemical and/or biomolecular species in the analyte can be achieved with multiple arrays A1, A2, A3, etc., of multiple sensors 5 wherein the sensor membranes of different arrays A1, A2, A3, etc. are coated with different chemical/biological binding sites. For example, as shown in FIG. 32, multiple sensors 5 of array A1 can have their sensor membranes 12 each coated with a coating A, while sensors 5 of array A2 can have their sensor membranes coated with a coating B, and so on for the other arrays by a robotic stamping, a technique currently used for fabricating DNA microarray sample. Multiple detection of multiple chemical and/or biomolecular species thereby can be obtained for one analyte in one experiment.

Figure 33C:
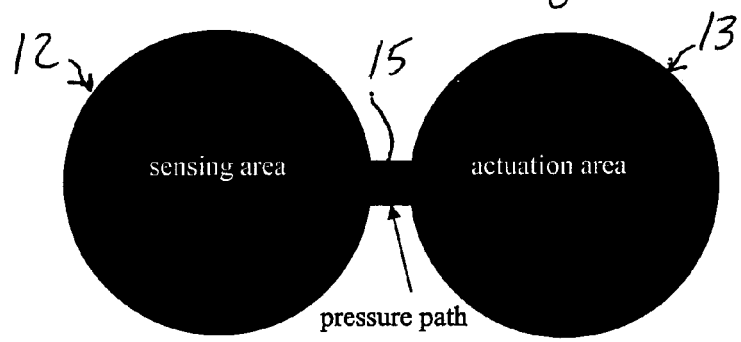
FIG. 33c is a schematic plan view of the sensor area and actuation area.

Pressure Control-Mechanism:

Referring to FIGS. 33a, 33b, and 33c, these figures illustrate an aspect of the invention for inflating the thin elastomeric membrane 12 to provide the small internal gas pressure (10–1000 Pa) described above to impart the dome shape to the thin membrane 12. Pursuant to this aspect of the invention, a sensor comprises a pair of thin membranes 12 and 13 wherein one of the membranes constitutes a functional membrane 12 separated from the substrate 10 by a space or gap 12g as described above and the other membrane 13 constitutes an actuation or pump membrane that also is separated by a space or gap 13g from the substrate 10 and is movable relative to the substrate 10 to force a gas, such as air, residing in space or gap 13g under desired pressure into space or gap 12g to apply the internal gas pressure P described on the inner side 12b of the membrane 12 to impart and maintain the dome shape thereto. A passage 15 interconnects and communicates the spaces or gap 12g with the space or gap 13g to this end. The actuation membrane 13 is caused to move toward the substrate 10 by application of electrostatic force by a suitable voltage between electrode 17 on or a part of the membrane 13 and electrode 19 on or beneath the surface of the substrate 10 as shown in FIG. 33b. Electrodes 17, 19 are connected by lead wires to a suitable power source shown to this end. Control of the actuation or pump membrane 13 can be effected using a feedback loop that compares a measured capacitance value of the sensor 5 (having functional membrane 12) to a desired reference capacitance value selected for conducting a particular analyte analysis and commands actuation of the actuation or pump membrane 13 when the measured capacitance differs from the reference value. The feedback loop can be incorporated in a CMOS or other solid state circuit.

The invention envisions the use of other internal pressurization techniques to apply the internal gas pressure on the membrane inner surface 12b. For example, such pressurization techniques can include the use of a capillary tube connected to reaction chamber, gas flow through an aperture in the substrate into the gap or space under the membrane, and other pressurization techniques.

Integration of Microfluidics:

In micro-cantilever detection systems, the time for reaction between the molecules in a liquid analyte solution and binding sites on the membrane surface 12b can be limited by diffusion of the molecules in the introduced analyte solution. This problem is effectively solved by the membrane configuration suggested in this invention because the membrane structure is inherently robust against the flow above it. When there is a flow over the membrane 12, the fluctuation due to small pressure change will be quickly damped out. Therefore, the internal flow of liquid analyte can be induced over the membrane 12 to enhance the mixing. The detection time, in this case, is limited by reaction, resulting in a drastic reduction in detection times. Furthermore, the mixing flow of the analyte solution can be induced by using sensors of the type shown in FIG. 33b arranged in an array and energizing the electrostatic actuation membranes 13 of the sensors to provide a fluid mixing flow around the detection area. Alternatively or in addition, even the sensing membranes 12 can be used for inducing internal mixing flow. Peristaltic pumping mechanism optionally also can be used for inducing mixing flow of the liquid analyte solution.

EXAMPLE 1

Self-Supporting Dome-Shaped Thin Membrane

An elastomeric thin membrane 12 having a self-supporting dome shape can be fabricated in practice of the invention to avoid the need to apply internal gas pressure surface on the inner membrane surface 12b as mentioned above. Referring to FIGS. 34a–34c, the method of fabrication involves low pressure chemical vapor deposition of a $Si_3Ni_4$ layer to a thickness of 200 nm on a Si wafer followed by patterning a square opening and then KOH anisotropic etching to remove the Si wafer in the square area, FIG. 34a. Then, PDMS material is spin coated at 3000 rpm for 3 minutes to form a flat, thin film (12 micron thick) atop the $Si_3Ni_4$ layer, FIG. 34a. The coated PDMS is baked at 100 degrees C. for one hour to evaporate the solvent. In order to suspend baked the PDMS membrane, the $Si_3Ni_4$ layer is etched by reactive ion etching (RIE) for 2 minutes using $CF_4$ gas plus $O_2$ gas, FIG. 34b. The suspended PDMS membrane is thermally deflected to a dome shape, FIG. 34c, as it is heated during deposition of one or more metallic layers thereon. The one or more metallic (Ti/Au and Al) layers are evaporated from appropriate sources by use of an electron beam in a high vacuum ($10^{-7}$ torr) such that the metallic layers are deposited on the membrane, FIG. 34c. When the membrane cools down to room temperature, the membrane wants to shrink down, but is constrained by the deposited metal layer(s) to maintain the dome shape imparted by the thermal deflection.

The amount of constrained deflection of the membrane depends on the stress and thickness of the metallic layer(s) applied. For example, a Ti inner layer and then Au outer layer of respective 8 nm and 20 nm thickness were deposited on the bottom side of the membrane in FIG. 34c using an electron beam evaporator proximate that side. A deflection of the membrane of a few hundred microns was observed following deposition of the Ti and Au layers and cooling to room temperature. On the other hand, when an Al layer of 25 nm thickness was then deposited on the top side of the membrane (after the Ti and Au layers were deposited on the bottom side in FIG. 34c), the membrane deflection decreased to 20 microns to fine tune the dome shape; i.e. its radius of curvature. A thicker Al layer can be deposited to further reduce the deflection, or even reverse it. The final dome shaped PDMS membrane of FIG. 34c thus includes the Ti and Au layers on the bottom side and the Al layer on the top side of the PDMS membrane. FIG. 34d shows a glass plate substrate having a Cr layer and Au layer forming an electrode thereon and disposed on the PDMS membrane periphery in a manner that the Au layer electrode faces the thin membrane and its electrode to form a sensor. The peripheral edges of the glass plate substrate are adhered to the opposing peripheral edges of the thin membrane.

The above-described fabrication process is useful for a free-standing soft membrane comprising PDMS which has a low Young's modulus (750 kPa) and thus is extremely sensitive to stress variations. The PDMS membrane is formed in a dome shape after Ti/Au evaporation due to thermal stress mismatching during the deposition. The formation of the dome-shaped membrane is particularly important when both the tensile and compressive surface stresses need to be measured by a clamped membrane.

Such a thin membrane sensor was demonstrated to provide a high-sensitivity, label-free detection of a bioaffinity reaction (biotin-streptavidin). For example, biotin was immobilized on the gold surface of the outer gold layer of the dome shaped membrane using cysteamine and photobiotin. Streptavidin in phosphate bsuffered saline (PBS) was added to monitor the reaction. Referring to FIG. 35, when streptavidin (10 aM) was added, the capacitance of the sensor exponentially decreased over time due to the inflation of membrane by compressive surface stress produced by the chemical reaction. Steady state was reached in less than 5 minutes. This high sensitivity and quick response are ascribed to especially strong biotin-streptavidin reaction. This manifests the power of the thin membrane sensor that can interpret a reaction through molecular binding force, which is fundamentally different from tagging-based approaches. When more analyte at a higher concentration was added at 1500 seconds, a further decrease in the capacitance was observed.

EXAMPLE 2

Hard Silicon Nitride Thin Membrane

A fabrication process for a hard flat membrane device is illustrated in FIG. 36a–36d. The capacitive gap (100 nm) was controlled by the depth (e.g. 350 nm) of the trench formed in a Si wafer by RIE as shown in FIG. 36a, and the thickness of the $Si_3N_4$ membrane and the Al layer, FIG. 36c. The $Si_3N_4$ membrane is deposited on surfaces of the Si wafer by chemical vapor deposition, FIG. 36b. A recess or well is formed in the wafer by KOH etching and patterning of the one $Si_3N_4$ membrane layer as shown in FIG. 36b. Layers of Ti and then Au are vapor deposited on surfaces of the well and the thin membrane as shown in FIG. 36c and as described in Example 1. An electrode layer of Al is vapor deposited on the opposite surface of the thin membrane as also shown in FIG. 36b. The metallic layers vapor deposited on the $Si_3N_4$ membrane are believed to induce surface stress on the $Si_3N_4$ membrane layer in a manner to impart and maintain a slight dome membrane shape extending in a direction toward the Ti and Au layers (similar to and less pronounced than that of FIG. 34c) but not shown in FIGS. 36c or 36d for convenience. A PYREX glass substrate having an Al electrode layer thereon facing the Al electrode layer on the $Si_3N_4$ membrane is bonded to the Si wafer by anodic bonding to form a sensor. Thicknesses of the $Si_3N_4$ membrane and the metallic layers and electrode spacing are shown in nanometers (nm) in FIGS. 36b–36d.

FIG. 37 shows the detection result of a SAM (self-assembled monolayer) formed or deposited on the $Si_3N_4$ membrane coated with the gold (Au) outer reaction layer or surface, FIG. 36d. A solution of 1-hexadecanethiol 92% was introduced into the well with the well facing upwardly by inverting the sensor of FIG. 36d. The capacitance change was monitored using a precision capacitance meter. The capacitance increase (~40fF) is attributed to the compressive surface stress and resulting deflection caused by the SAM formed on the gold surface. The measurement with a droplet of water also shown in FIG. 37 shows that the response is not due to other effects such as mass or liquid temperature.

Figure 38:
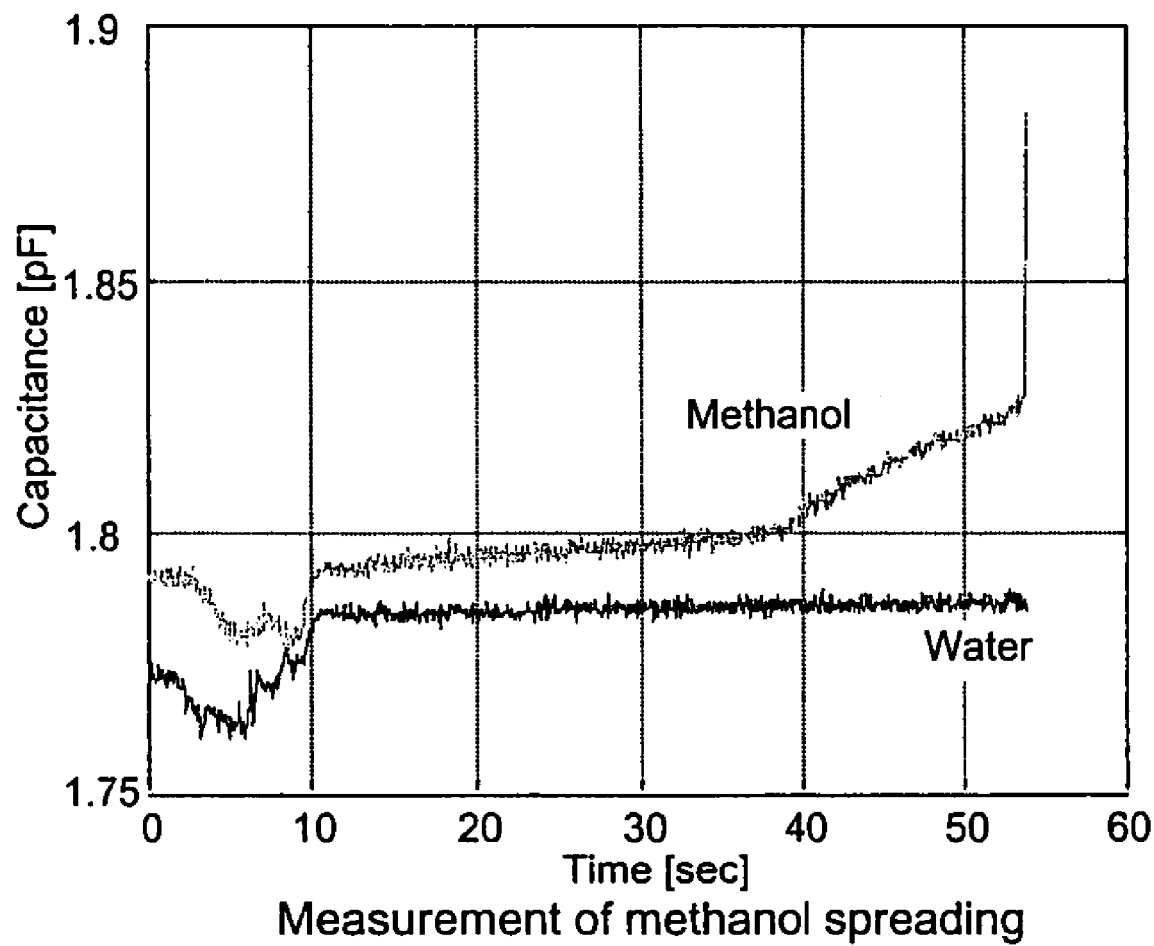
FIG. 38 is a graph of capacitance of the prototype sensor of FIG. 36d versus time during measurement of methanol spreading.

Referring to FIG. 38, a tensile surface stress was detected after a small droplet of methanol (hydrophobic) was placed in the well. As a result of a fast spreading of the methanol on the fresh hydrophobic gold outer surface, a huge capacitance increase was observed, FIG. 38. On the other hand, the water (hydrophilic) hardly caused any change, consistent with the observation that the droplet remained unspread on the gold.

Although the invention has been described with respect to certain embodiments thereof, those skilled in the art will appreciate that changes and modifications to the embodiments can be made within the spirit and scope of the invention as set forth in the appended claims.

We claim:

1. A sensor, comprising a substrate and a membrane connected to said substrate and having a membrane surface, said membrane surface having a coating comprising a reaction agent for interacting with a medium in a manner to deflect said membrane relative to said substrate, a first electrode on the substrate and spaced from the membrane, and a second electrode on or a part of the membrane and from which first electrode and second electrode a capacitance measurement can be made.

2. The sensor of claim 1 wherein said membrane has a convex or concave shape before said interacting.

3. The sensor of claim 1 wherein said surface has a chemical or biomolecular reaction agent thereon such that a reaction with species of an analyte occurs on said surface in a manner to deflect said membrane relative to said substrate.

4. The sensor of claim 1 wherein said membrane has a deflectable convex or concave shape before said interacting.

5. The sensor of claim 1 wherein the coating includes reaction molecules.

6. The sensor of claim 5 wherein the molecules provide chemical reaction sites.

7. The sensor of claim 5 wherein the molecules provide biomolecular reaction sites.

8. The sensor of claim 1 wherein the membrane includes an interior surface subjected to gas pressure to inflate the membrane to a convex shape and an exterior surface having the reaction agent thereon such that a reaction with species of an analyte occurs on said exterior surface in a manner to deflect said membrane relative to said substrate while said membrane has said convex shape imparted thereto by gas pressure inflation.

9. The sensor of claim 1 wherein the membrane is an elastomeric material.

10. The sensor of claim 1 wherein the membrane includes one or more metallic layers imparting a convex or concave shape to said membrane before said interacting.

11. The sensor of claim 1 wherein the membrane comprises a ceramic material.

12. The sensor of claim 11 wherein the ceramic material comprises silicon oxide or silicon nitride.

13. The sensor of claim 1 wherein the medium comprises an analyte.

14. A sensor, comprising a sensor area having a membrane on a substrate according to claim 1 and an actuation area in gas flow communication with the sensor area and having an actuation membrane spaced from the substrate by a gas containing gap and movable in a manner to gas pressurize said sensor area when said actuation membrane is moved toward said substrate.

15. The sensor of claim 1 having said surface on which the reaction agent interacts with a liquid or gas medium in a manner to deflect said membrane relative to said substrate.

16. A sensor comprising a substrate and a membrane connected to said substrate and having a surface with a coating comprising a reaction agent for interacting with a medium a manner to deflect said membrane relative to said substrate, a first electrode on the substrate and spaced from the membrane, and a second electrode on or a part of the membrane and from which first electrode and second electrode a capacitance measurement can be made, and further having a dummy membrane connected to the substrate and having a surface on which no interaction with said medium occurs, a third electrode on the substrate spaced from the dummy membrane, and a fourth electrode on or a part of the dummy membrane and from which third electrode and fourth electrode a capacitance measurement can be made.

17. A transducer, comprising a substrate and a membrane having a surface with a coating comprising a reaction agent and peripherally connected to said substrate and being deflectable relative to said substrate by an interaction of the reaction agent with a medium occurring on said membrane surface, a first electrode on the substrate and spaced from the membrane, and a second electrode on or part of the membrane and from which first electrode and second electrode a capacitance measurement can be made.

18. A method of sensing, comprising producing an interaction between a medium and a reaction agent of a coating on a surface of a membrane connected to a substrate, deflecting the membrane in response to the interaction, and detecting the deflection of the membrane by measuring a change in capacitance between a first electrode on the substrate and a second electrode on or a part of the membrane.

19. The method of claim 18 wherein said interaction comprises a chemical and/or biomolecular reaction between an agent on said surface and molecules in an analyte.

20. A method of sensing, comprising producing an interaction between a medium and a reaction agent of a coating on a surface of a membrane connected to a substrate while said membrane is inflated by gas pressure to impart a deflectable shape thereto, deflecting the membrane in response to the interaction, and detecting the deflection of the membrane by measuring a change in capacitance between a first electrode on the substrate and a second electrode on or a part of the membrane.

* * * * *

UNITED STATES PATENT AND TRADEMARK OFFICE
CERTIFICATE OF CORRECTION

PATENT NO. : 7,086,288 B2 Page 1 of 1
APPLICATION NO. : 10/723307
DATED : August 8, 2006
INVENTOR(S) : Junghoon Lee et al.

It is certified that error appears in the above-identified patent and that said Letters Patent is hereby corrected as shown below:

Column 19, line 52; add -- - -- after "gas".
Column 20, line 10; add --in-- between "medium" and "a". Should read -- medium in a manner--

Signed and Sealed this

Twenty-seventh Day of March, 2007

JON W. DUDAS
*Director of the United States Patent and Trademark Office*